US010261475B1

(12) United States Patent
Kahn et al.

(10) Patent No.: US 10,261,475 B1
(45) Date of Patent: *Apr. 16, 2019

(54) SMART WATCH EXTENDED SYSTEM

(71) Applicant: DP Technologies, Inc., Scotts Valley, CA (US)

(72) Inventors: Philippe R. Kahn, Santa Cruz, CA (US); Arthur Kinsolving, Santa Cruz, CA (US); David Vogel, Santa Cruz, CA (US); Mark Andrew Christensen, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/458,936

(22) Filed: Mar. 14, 2017

Related U.S. Application Data

(63) Continuation of application No. 14/630,547, filed on Feb. 24, 2015, now Pat. No. 9,594,354, which is a
(Continued)

(51) Int. Cl.
*G04B 47/06* (2006.01)
*G04G 21/00* (2010.01)
(Continued)

(52) U.S. Cl.
CPC .......... *G04B 47/063* (2013.01); *A61B 5/1118* (2013.01); *A61B 5/4806* (2013.01);
(Continued)

(58) Field of Classification Search
CPC ...... G04G 21/00; G04G 21/025; G04G 99/00; G04B 47/063; A61B 5/1118; A61B 5/4806; A61B 5/681; A61B 5/742
(Continued)

(56) References Cited

U.S. PATENT DOCUMENTS 2,082,843 A   6/1937  Mathez
3,541,781 A  11/1970  Bloom
(Continued)

FOREIGN PATENT DOCUMENTS

AU  2003203967     11/2004
CH      377738 A    1/1964
(Continued)

OTHER PUBLICATIONS

"Fitbit Product Manual," <http://www.fitbit.com/manual>, Last updated Mar. 29, 2010, 20 pages.
(Continued)

*Primary Examiner* — Edwin A. Leon
(74) *Attorney, Agent, or Firm* — HIPLegal LLP; Judith Szepesi

(57) ABSTRACT

A method and apparatus to provide an extended band is described. The method comprises pairing a watch and a host device. The method further comprises monitoring a user's status with a plurality of sensors on the host device and/or the watch, and using the extended band to do one or more of: provide alerts to the user, based on the sensor data, control the extended band from one of the devices, and share data with third parties using the extended band.

20 Claims, 15 Drawing Sheets

Related U.S. Application Data continuation-in-part of application No. 14/255,923, filed on Apr. 17, 2014.

(60) Provisional application No. 61/814,178, filed on Apr. 19, 2013.

(51) Int. Cl.

| | |
|---|---|
| *A61B 5/11* | (2006.01) |
| *A61B 5/00* | (2006.01) |
| *G04G 9/00* | (2006.01) |
| *G04G 21/04* | (2013.01) |
| *G06F 1/16* | (2006.01) |
| *A61B 5/01* | (2006.01) |
| *A61B 5/024* | (2006.01) |
| *A61B 5/145* | (2006.01) |

(52) U.S. Cl.
CPC .............. *A61B 5/681* (2013.01); *A61B 5/742* (2013.01); *G04G 9/0064* (2013.01); *G04G 21/00* (2013.01); *G04G 21/04* (2013.01); *G06F 1/163* (2013.01); *A61B 5/01* (2013.01); *A61B 5/02438* (2013.01); *A61B 5/11* (2013.01); *A61B 5/14532* (2013.01); *A61B 5/14542* (2013.01); *A61B 2562/0219* (2013.01); *A61B 2562/0271* (2013.01)

(58) Field of Classification Search
USPC .......................................... 368/10, 250–251
See application file for complete search history.

(56) References Cited

U.S. PATENT DOCUMENTS

| | | | |
|---|---|---|---|
| 4,322,609 A | 3/1982 | Kato | |
| 6,547,728 B1 | 4/2003 | Cornuejols | |
| 6,556,222 B1* | 4/2003 | Narayanaswami | G04G 9/0064 368/295 |
| 6,834,436 B2 | 12/2004 | Townsend et al. | |
| 7,862,226 B2 | 1/2011 | Bracher et al. | |
| 9,448,536 B1 | 9/2016 | Kahn et al. | |
| 9,474,876 B1 | 10/2016 | Kahn et al. | |
| 9,594,354 B1* | 3/2017 | Kahn ...................... G04G 21/00 | |
| 2002/0080035 A1 | 6/2002 | Youdenko | |
| 2003/0095476 A1 | 5/2003 | Mollicone et al. | |
| 2003/0204412 A1 | 10/2003 | Brier | |
| 2003/0231495 A1 | 12/2003 | Searfoss | |
| 2004/0034289 A1 | 2/2004 | Teller et al. | |
| 2004/0049132 A1 | 3/2004 | Barron et al. | |
| 2004/0133081 A1 | 7/2004 | Teller et al. | |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0075116 A1 | 4/2005 | Laird et al. | |
| 2005/0143617 A1 | 6/2005 | Auphan | |
| 2005/0154330 A1 | 7/2005 | Loree | |
| 2005/0190065 A1 | 9/2005 | Ronnholm | |
| 2005/0237479 A1 | 10/2005 | Rose | |
| 2005/0245793 A1 | 11/2005 | Hilton et al. | |
| 2005/0288904 A1 | 12/2005 | Warrior et al. | |
| 2006/0025299 A1 | 2/2006 | Miller et al. | |
| 2006/0064037 A1 | 3/2006 | Shalon et al. | |
| 2006/0097884 A1 | 5/2006 | Jang et al. | |
| 2006/0150734 A1 | 7/2006 | Mimnagh-Kelleher et al. | |
| 2006/0252999 A1 | 11/2006 | DeVaul et al. | |
| 2006/0266356 A1 | 11/2006 | Sotos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0191692 A1 | 8/2007 | Hsu et al. | |
| 2007/0251997 A1 | 11/2007 | Brown et al. | |
| 2007/0287930 A1 | 12/2007 | Sutton | |
| 2008/0062818 A1* | 3/2008 | Plancon ............... G04B 19/082 368/10 |
| 2008/0125820 A1 | 5/2008 | Stahmann et al. | |
| 2008/0191885 A1 | 8/2008 | Iv et al. | |
| 2008/0234785 A1 | 9/2008 | Nakayama et al. | |
| 2009/0030767 A1 | 1/2009 | Morris et al. | |
| 2009/0048540 A1 | 2/2009 | Otto et al. | |
| 2009/0069644 A1 | 3/2009 | Hsu et al. | |
| 2009/0082699 A1 | 3/2009 | Bang et al. | |
| 2009/0105785 A1 | 4/2009 | Wei et al. | |
| 2009/0121826 A1 | 5/2009 | Song et al. | |
| 2009/0128487 A1 | 5/2009 | Langereis et al. | |
| 2009/0143636 A1 | 6/2009 | Mullen et al. | |
| 2009/0177327 A1 | 7/2009 | Turner et al. | |
| 2009/0203970 A1 | 8/2009 | Fukushima et al. | |
| 2009/0207028 A1 | 8/2009 | Kubey et al. | |
| 2009/0227888 A1 | 9/2009 | Salmi et al. | |
| 2009/0264789 A1 | 10/2009 | Molnar et al. | |
| 2010/0010330 A1 | 1/2010 | Rankers et al. | |
| 2010/0061596 A1 | 3/2010 | Mostafavi et al. | |
| 2010/0075807 A1 | 3/2010 | Hwang et al. | |
| 2010/0079291 A1 | 4/2010 | Kroll et al. | |
| 2010/0079294 A1 | 4/2010 | Rai et al. | |
| 2010/0083968 A1 | 4/2010 | Wondka et al. | |
| 2010/0100004 A1 | 4/2010 | Someren | |
| 2010/0102971 A1 | 4/2010 | Virtanen et al. | |
| 2010/0152543 A1 | 6/2010 | Heneghan et al. | |
| 2010/0152546 A1 | 6/2010 | Behan et al. | |
| 2010/0256512 A1 | 10/2010 | Sullivan | |
| 2010/0331145 A1 | 12/2010 | Lakovic et al. | |
| 2011/0015467 A1 | 1/2011 | Dothie et al. | |
| 2011/0015495 A1 | 1/2011 | Dothie et al. | |
| 2011/0018720 A1 | 1/2011 | Rai et al. | |
| 2011/0058456 A1 | 3/2011 | De et al. | |
| 2011/0137836 A1 | 6/2011 | Kuriyama et al. | |
| 2011/0160619 A1 | 6/2011 | Gabara | |
| 2011/0190594 A1 | 8/2011 | Heit et al. | |
| 2011/0199218 A1 | 8/2011 | Caldwell et al. | |
| 2011/0230790 A1 | 9/2011 | Kozlov | |
| 2011/0295083 A1 | 12/2011 | Doelling et al. | |
| 2012/0083715 A1 | 4/2012 | Yuen et al. | |
| 2012/0232414 A1 | 9/2012 | Mollicone et al. | |
| 2012/0243379 A1 | 9/2012 | Balli | |
| 2012/0253220 A1 | 10/2012 | Rai et al. | |
| 2013/0018284 A1 | 1/2013 | Kahn et al. | |
| 2013/0053656 A1 | 2/2013 | Mollicone et al. | |
| 2013/0286793 A1 | 10/2013 | Umamoto | |
| 2013/0289419 A1 | 10/2013 | Berezhnyy et al. | |
| 2014/0005502 A1 | 1/2014 | Klap et al. | |
| 2014/0085077 A1 | 3/2014 | Luna et al. | |
| 2014/0200691 A1 | 7/2014 | Lee et al. | |
| 2014/0219064 A1 | 8/2014 | Filipi et al. | |
| 2014/0232558 A1 | 8/2014 | Park et al. | |
| 2014/0256227 A1 | 9/2014 | Aoki et al. | |
| 2014/0276227 A1 | 9/2014 | Pérez | |
| 2014/0288878 A1 | 9/2014 | Donaldson | |
| 2015/0085622 A1 | 3/2015 | Carreel et al. | |
| 2015/0098309 A1* | 4/2015 | Adams ................. G04G 9/0064 368/10 |
| 2015/0289802 A1 | 10/2015 | Thomas et al. | |
| 2017/0003666 A1 | 1/2017 | Nunn et al. | |

FOREIGN PATENT DOCUMENTS

| | | |
|---|---|---|
| CH | 668349 A | 12/1988 |
| CH | 697528 B1 | 11/2008 |
| DE | 19642316 A1 | 4/1998 |
| EP | 1139187 B1 | 10/2010 |
| JP | 8160172 | 6/1996 |
| JP | 2007132581 A | 5/2007 |
| KR | 1020009085403 | 6/2011 |
| KR | 1020100022217 | 3/2012 |
| WO | 2008038288 A3 | 5/2009 |

OTHER PUBLICATIONS

"How BodyMedia Fit Works", <http://www.bodymedia.com/Shop/Learn-More/How-it-works, accessed Jun. 17, 2011, 2 pages.

(56) References Cited

OTHER PUBLICATIONS

"Power Nap," <en.wikipedia.org/wiki/Powersub.-nap>, Last Modified Sep. 20, 2012, 4 pages.
"Sara Mednick," <en.wikipedia.org/wiki/Sara.sub.-Mednick>, Last Modified Sep. 12, 2012, 2 pages.
"Sleep Debt," <en.wikipedia.org/wiki/Sleep.sub.--debt>, Last Modified Aug. 25, 2012, 3 pages.
"Sleep Inertia," <en.wikipedia.org/wiki/Sleep.sub.--inertia, Last Modified Sep. 12, 2012, 2 pages.
"Sleep," <en.wikipedia.org/wiki/Sleep.sub.-stages#Physiology>, Last Modified Oct. 5, 2012, 21 pages.
"Slow Wave Sleep," <en.wikipedia.org/wiki/Slow-wave.sub.-sleep>, Last Modified Jul. 22, 2012, 4 pages.
Actigraphy, From Wikipedia, the free encyclopedia, downloaded at: http://en.wikipedia.org/wiki/Actigraphy on Apr. 24, 2014, 4 pages.
David F. Dinges, <en.wikipedia.org/wiki/David_Dinges>, Last Modified Sep. 12, 2012, 2 pages.
Desai, Rajiv, The Sleep, Archive for Mar. 2011, Dr. Rajiv Desai Blog, Mar. 17, 2011, 46 pages.
Jaines, Kira, "Music to Help You Fall Sleep," <http://www.livestrong.com/article/119802-music-fall-sleep/>, May 10, 2010, 2 pages.
Jetlog Reviewers Guide, <http://wwwjetlog.com/fileadmin/Presse.sub.-us/24x7ReviewersGuide.pdf- >, 2009, 5 pages.
Lichstein, et al., Actigraphy Validation with Insomnia, SLEEP, vol. 29, No. 2, 2006, pp. 232-239.
Liden, Craig B, et al, "Characterization and Implications of the Sensors Incorporated into the SenseWear(TM) Armband for Energy Expenditure and Activity Detection", <http://www.bodymedia.com/Professionals/Whitepapers/Characterization-and-Implications-of-the-Sensors-Incorporated-into-the-SenseWear>, accessed Jun. 17, 2011, 7 pages.
Patel, et al., Validation of Basis Science Advanced Sleep Analysis, Estimation of Sleep Stages and Sleep Duration, Basis Science, San Francisco, CA, Jan. 2014, 6 pages.

PCT Application No. PCT/US2012/46477, Search History, Date of Search Sep. 12, 2012, 3 pages.
PCT/US2012/046477, International Search Report and Written Opinion, dated Sep. 28, 2012, 10 pages.
PCT/US2012/069326, International Preliminary Report on Patentability, Jun. 17, 2014, 7 pages.
PCT/US2012/069326, International Search Report, dated May 30, 2013, 3 pages.
PCT/US2012/069326, Written Opinion of the International Searching Authority, dated May 30, 2013, 6 pages.
PCT/US2013/028939, International Preliminary Report on Patentability, dated Jan. 23, 2014, 8 pages.
PCT/US2013/028939, International Search Report, dated May 10, 2013, 10 pages.
PCT/YS2013/028939, International Preliminary Report on Patentability, dated May 10, 2013, 6 pages.
Pires, P. D. C. Activity Characterization from Actimetry Sensor Data for Sleep Disorders Diagnosis, Universidade Técnica de Lisboa, Sep. 2008, 10 pages.
Pollak, et al., How Accurately Does Wrist Actigraphy Identify the States of Sleep and Wakefulness?, Actigraphy and Sleep, SLEEP, vol. 24, No. 8, 2001, pp. 957-965.
PowerNap iPhone App, <http://forums.precentral.net/webos-apps-software/223091-my-second-app--powernap-out-app-catalog-nap-timer.html>, Jan. 6, 2010, 10 pages.
Sound-Remedies.com: Sonic Solutions for Health, Learning & Productivity, <http://www.sound-remedies.com/ammusforslee.html>, Accessed May 23, 2013, 2 pages.
Sunseri, Maria, et al, "The SenseWear (TM) Armband as a Sleep Detection Device," <http://sensewear.bodymedia.com/SenseWear-Studies/SW-Whitepapers/The-SenseWear-armband-as-a-Sleep-Detection-Device>, 2005, 9 pages.

\* cited by examiner

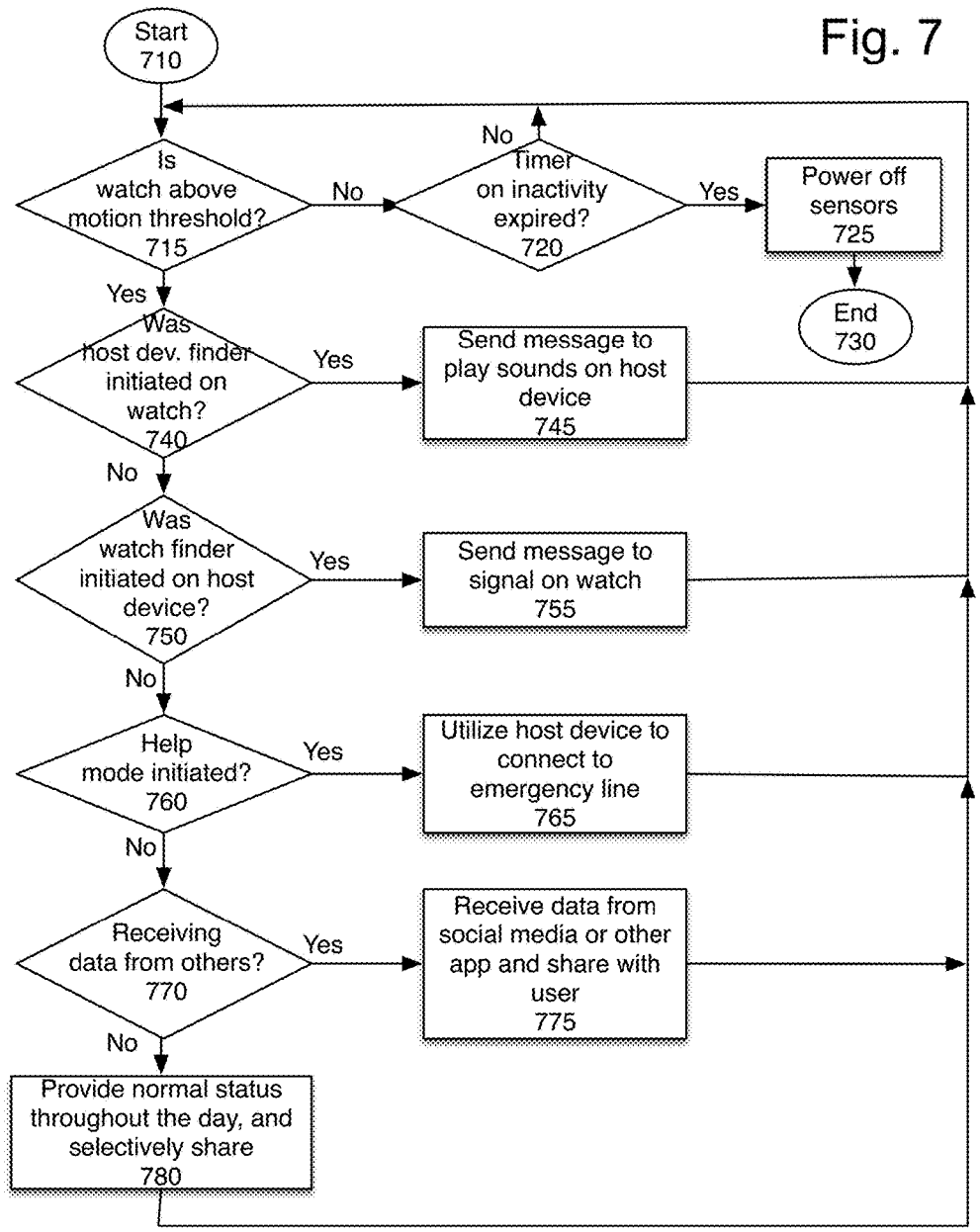

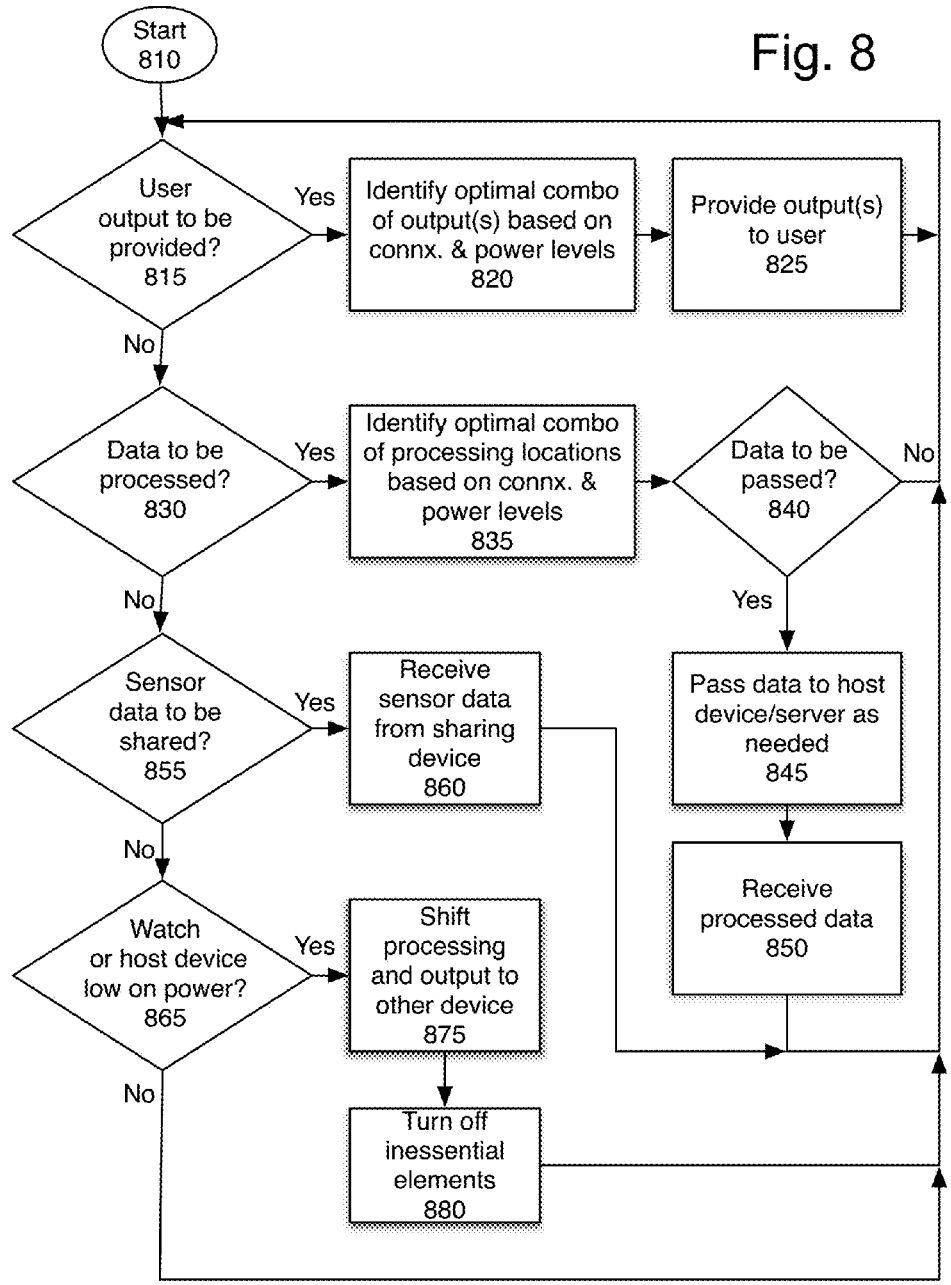

| | Watch | Mobile Device |
|---|---|---|
| Get Active Alerts (inactivity alerts) | vibration | audible alert or text |
| Sleep session started/in-progress | Point to sleep state indicator | Chart of sleep state status |
| PowerNap started/in-progress | Point to sleep state indicator | Power nap display, with time count-down |
| Put watch sensors to sleep | Push button in pattern | Use visual menu/icon |
| Wake watch sensors up | Perform gesture command | use visual menu/icon |
| Waking up user | vibration | Audio alarm, optionally user's perferred music |
| Getting ready for sleep | Push crown to move to sleep state | Home automation controls to ready space for sleep |
| Display of activity level for the day | Percentage of goal steps achieved shown on dial | Chart showing activity level, goals, and status |
| Display of sleep efficiency | Percentage of goal sleep achieved shown on dial | Chart showing sleep levels, goals, and status. |

Fig. 9

SMART WATCH EXTENDED SYSTEM

RELATED APPLICATIONS

The present application is a continuation application of U.S. patent application Ser. No. 14/630,547, filed on Feb. 24, 2015, which claims priority to U.S. patent application Ser. No. 14/255,923, filed on Apr. 17, 2014, which claims priority to U.S. Provisional Application No. 61/814,178, filed on Apr. 19, 2013, all of which are incorporated herein by reference.

FIELD

The present invention relates to a smart watch, and more particularly to a smart watch extended system.

BACKGROUND

As accelerometers and other sensors are becoming more accurate, lower power, more cost-effective and smaller. There are numerous systems available, which enable a user to monitor his or her activity or sleep.

For example, there are pedometers or other activity monitors that track a user's activities to improve health. There are also some sleep monitors, which use accelerometers.

BRIEF DESCRIPTION OF THE FIGURES

The present invention is illustrated by way of example, and not by way of limitation, in the figures of the accompanying drawings and in which like reference numerals refer to similar elements and in which:

FIG. 7 is a flowchart of one embodiment of using the extended band.

FIG. 8 is a flowchart of one embodiment of shared processing on the extended band.

FIG. 9 is a table of some exemplary inputs and outputs using the extended band.

DETAILED DESCRIPTION

Figure 1A:
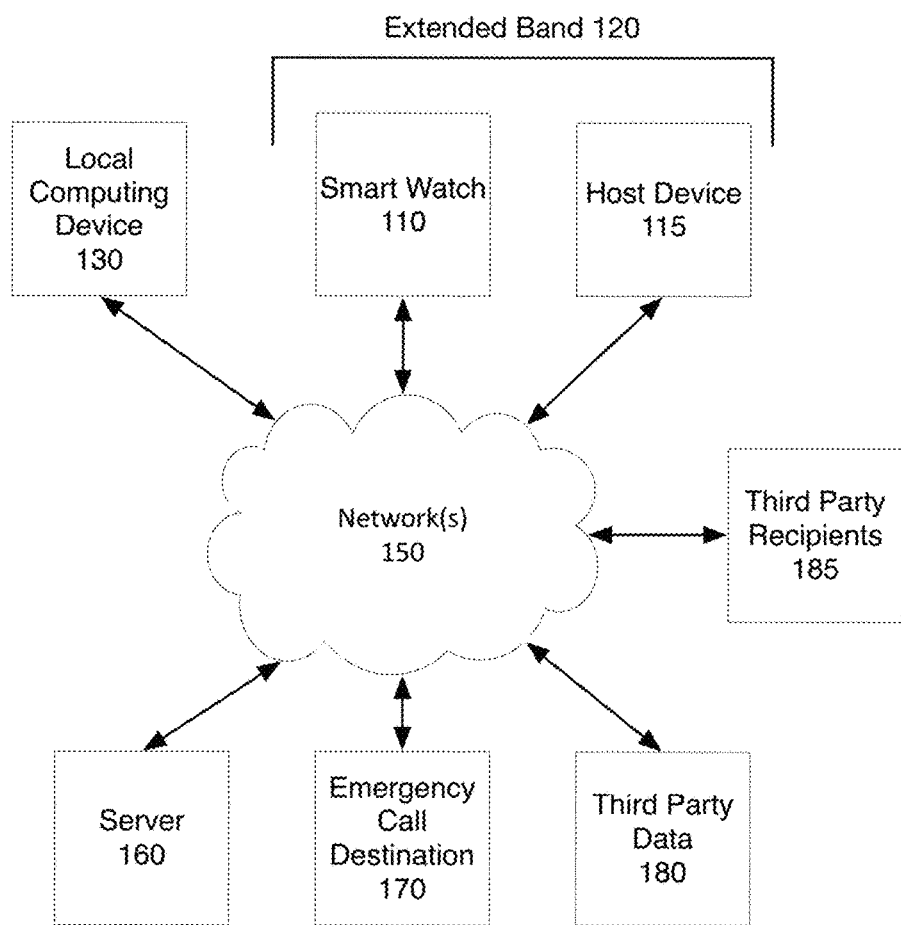
FIG. 1A is a block diagram of one embodiment of a system in which the present invention may be implemented.

The present invention is a smart watch extended system, also referred to as an extended band system, which is a combination of a smart watch including sensors and a computing device. The smart watch is designed to be worn by a user throughout the day and the night, in one embodiment. In one embodiment, the extended band system may include additional body-worn devices, or additional watches paired with the same computing device. In one embodiment, at least one sensor is worn or touched, placed next to on a soft surface, or carried by the user throughout the day. This enables the extended band to monitor the user's motions and other characteristics during the day and night. The tracking of sleep using actigraphy enables the detection of sleep phases and circadian rhythms. In one embodiment, the data obtained by the extended band may be used to track the user's activity level, create correlations between behaviors, and/or track various other health-related features, such as ergonomics, eating patterns, etc. The extended band provides useful feedback on the user's own status, and in one embodiment the status of others.

The system in the smart watch uses smart power management, and communication methods to enable the use of a smart watch 24 hours a day, without recharging the device for an extended period, such as a year or more. In one embodiment, a watch battery lasts over one year, for normal usage.

The extended band provides a MACS (Monitor, Alert, Control and Share) system. The system uses sensors on the band and/or the host device to Monitor the user's state. The system can provide Alerts on one or more component on the system, smart sleep cycle alarms, inactivity notifications, etc. The system also provides Control, enabling the user to control the band from the host device and vice-versa. The system also enables a user to Share data about themselves with others, through social media or directly with other users of the extended band system.

The smart watch includes one or more sensors, processors, and input/output elements. In one embodiment, the output of the smart watch uses mechanical movement with dials and hands, similar to a traditional watch, to display data to the user. In one embodiment, the output of the smart watch includes light emitting diodes (LEDs), in addition to dials and hands. This type of horological system provides a high fashion and high function system.

The computing device may be a mobile device such as a smart phone, or tablet computer, or desktop computer. The computing device may include one or more sensors, processors, and input/output elements. For simplicity, the computing device will be referred to as a host device in this Specification. Thus, the term "host device" should be interpreted as any computing device that can establish a sporadic or continuous connection with the smart watch.

The smart watch and host device, in one embodiment, maintain their connection most of the time that the devices are in range, thereby forming the extended band, consisting of the smart watch(es) and related host device(s). In another embodiment, the smart watch periodically sends its data to the host device. In another embodiment, the smart watch sends the data to the host device upon request by the user.

The extended band is able to use the combination of sensors to get more accurate data, and to leverage the rich user interface of the host device (speakers, large screen, vibrations, etc.). This enables the extended band, and the system as a whole, to optionally use the host device for real-time feedback to the user. Furthermore, sensors in the host device may add additional data to the system. Additionally, by controlling the band from the host device, the user interface provides a lot more opportunities, and the user has more fine-grained control. On the other side, by controlling the host device from the band, the system provides always-in-hand control for the host device.

For example, in one embodiment the smart watch can notify the host device that it is time to wake-up the user, then an application on the host device can play sounds to wake-up the user. These sounds can gently fade-up and be user selectable. In one embodiment, the smart watch may wake the user directly, using a vibration.

If the host device is connected to a home automation system, it can turn on lights, raise shades, start the coffee maker, etc. Because the host device is designed to be regularly charged, it can be much less power-conscious than a band designed to be worn for a longer time before recharging.

In this system, in one embodiment, the smart watch and the host device become essentially extensions of each other, and all features of the host device can be used for real-time monitoring, alert, control, and sharing. Similar, the smart watch may be used to provide monitoring, alerts, control, and sharing. For example if the host device is out of range (e.g. left behind), or, if the host device is a smartphone, when a call is received, the smart watch can control the host device, or provide an alert to the user. In one embodiment, the smart watch may be used selectively for indicating a received call, e.g. when the phone is set to silent or the user is in a loud environment. In one embodiment, elements of the band's user interface and state can be controlled from the host device. For example, the smart watch can be put into sleep state from the host device. Thus, the host device becomes an extension of the smart watch and the smart watch an extension of the host device. In one embodiment, elements of the host device's user interface and state can be controlled by the smart watch, in turn. In one embodiment, the smart watch may be used to turn on the host's ringer, turn on and off sensors, or otherwise control the host device.

The following detailed description of embodiments of the invention make reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

FIG. 1A is a block diagram of one embodiment of a system in which the present invention may be implemented. The system includes a smart watch 110 and an associated host device 115. The smart watch 110 and host device 115 make up an extended band 120. Although only one smart watch 110 and host device 115 are shown as being associated as an extended band 120, in one embodiment, one or more smart watches or other body-worn devices may be paired with one or more host devices to form a single extended band. For example, the user may have a smart for daily wear, and an armband for sleeping. The host device 115 may be the user's smart phone, as well as the user's tablet, laptop, music player, and/or other device. Thus, in one embodiment, a smart watch may be paired to multiple hosts, and a host may be paired to multiple smart watches or other body-worn devices, in one embodiment. In one embodiment, if there are a plurality of host devices, the host devices communicate with each other. In one embodiment, the smart watches are host-agnostic, and able to pair with a variety of devices with a variety of operating systems and applications. In one embodiment, when there are multiple available body-worn devices, the system determines which one is being worn by the user, and utilizes data only from that one. The determination may be made based on movement data, temperature data or other information from the body-worn device. In one embodiment, the user may also add the information. In one embodiment, the system may be capable of having more than one active body-worn device at the same time. For example, a user may wear the smart watch, and also a separate bracelet band. In one embodiment, the system combines data from the sensors of the multiple devices in such an instance.

The extended band 120 may be coupled via a low bandwidth direct connection such as Bluetooth 4.0 or similar connection mechanism. In one embodiment, the connection between the smart watch 110 and host device 115 may be continuous, periodic, or sporadic. In one embodiment, the preferred connection is continuous, enabling the use of the host device 115 as the input and output for the smart watch 110, and enabling fine-grained control of the watch. The host device 115 may be coupled to a network 150, such as the Internet. In one embodiment, the smart watch 110 may be coupled to the network 150, such as the Internet. In one embodiment, the connection between a smart watch 110 and host device 115 may be through a network 150. This configuration still forms an extended band 120.

The extended band 120 may be coupled through the network 150 to a server 160. The server 160 may be a remote server or a local device that acts as a server. The server 160 may be used to collect data from multiple users/devices. In one embodiment, the network 150 may also enable use of third party data 180, or provision of data to third parties 185. In one embodiment, the network connection may also enable the extended band 120 to connect to an emergency destination 170.

In one embodiment, data from the extended band 120 may be shared with various third party recipients 185. The third party recipients 185 in one embodiment may include social networks, such as FACEBOOK®, TWITTER®, GOOGLE+®, PINTREST® or other social networks, blogs, websites set up for the purpose, such as a competition site set up by NIKE® or another extended band supporter, or other third party recipients 185.

In one embodiment, an extended band 120 may also share data with another user's extended band through network 150, without going through server 160 or third parties 185. In another embodiment, data may be shared through server 160 and/or third party recipients 185. For example, one user's post on TWITTER® or check-in on FOURSQUARE® may be received by another user's extended band 120, and shared with the user through the user interface provided by host device 115. As another example, the extended bands of both people may provide their data to a server 160, associated with supporting the extended bands. The server 160 may share the extended band data with other users, who are associated with the owner of the extended band. This association may be voluntary (e.g., friends or connections set up by the user), circumstantial (e.g., users competing in the same competition, or being matched for an event), locational (e.g. users participating in the same race, or being in proximity), or otherwise established. In one embodiment, the bands may share data directly, without using the server 185 as the intermediary, if the users are associated.

Figure 1B:
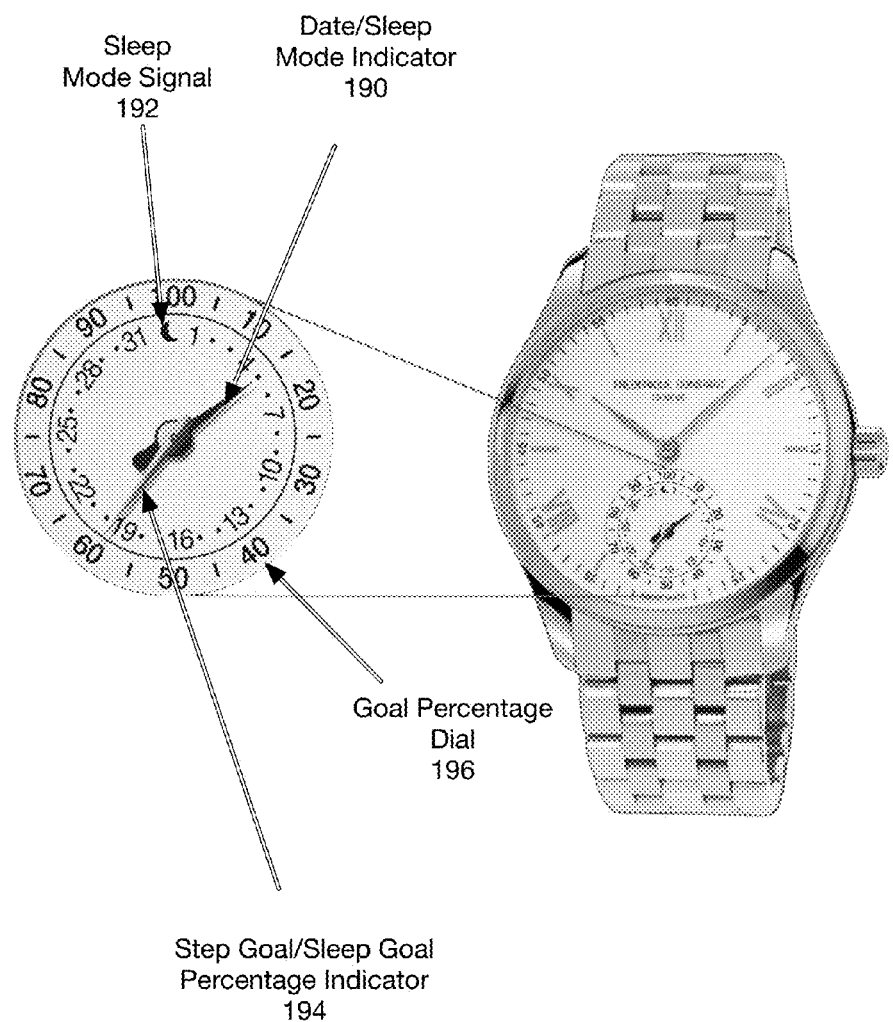
FIG. 1B-1C are images of an exemplary smart watches, which may be used the smart watch extended system.

FIG. 1B illustrates an exemplary appearance of a smart watch, in one embodiment of the present invention. The smart watch 110 includes a subdial to provide information to the user about the data obtained by the sensors. In one embodiment, the dial may be the same dial that shows the date, as illustrated in this figure. In one embodiment, the date indicator also becomes the sleep state indicator, here shown by a small moon at the top of the inner ring of numbers. The same dial and hand that shows the date during daytime hours is used to indicate sleep state for the monitoring, at night. In one embodiment, the user manually sets the sleep state indicator. In one embodiment the user inputs data to the smart watch using the crown push button. The outer ring of numbers reflects the step goal/sleep goal percentage, in one embodiment. During the day, the percentage of the step goals reached is shown (as can be seen the display is between 0 and 100%). At night, the percentage of the sleep goal reached is shown, again between 0 and 100%. In one embodiment, instead of a goal percentage, the actual step count may be displayed on a dial.

Figure 1C:
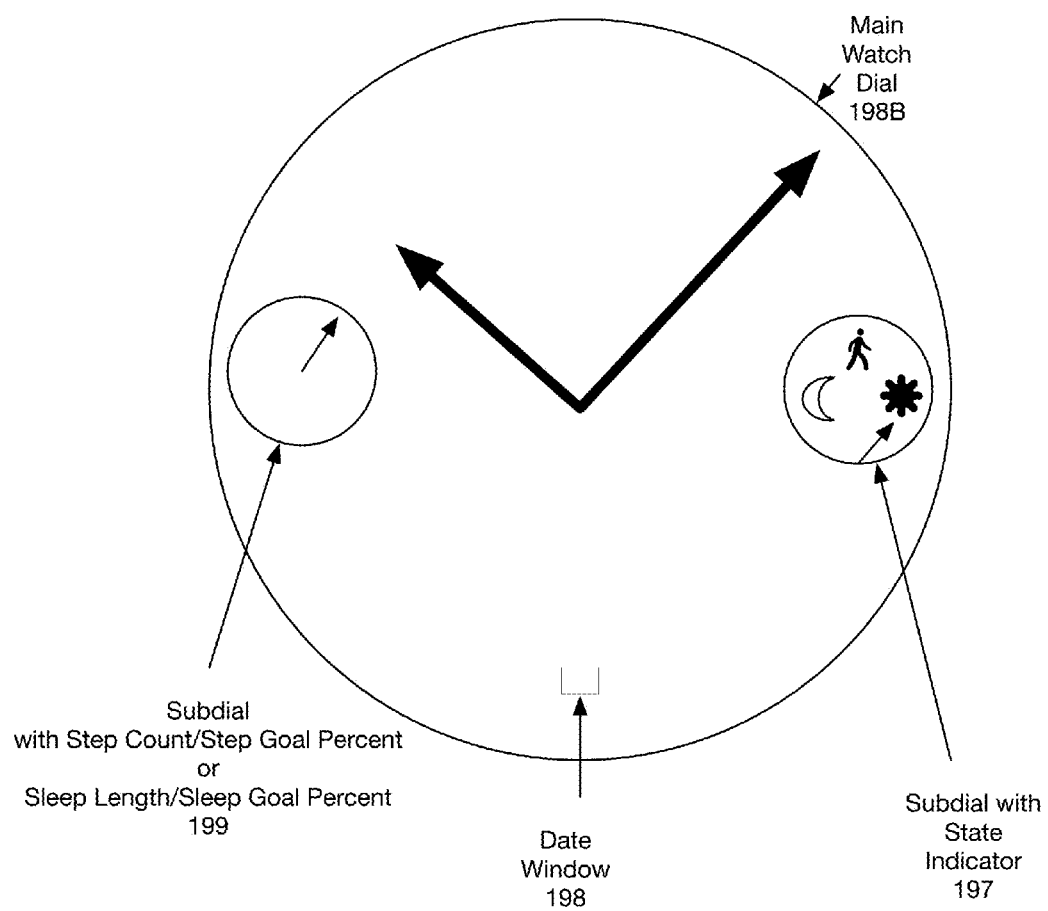

FIG. 1C illustrates another configuration of a watch face. Here, there are separate subdials for the state indicator 197, the step count/step percent or sleep count/sleep percent 199, and the date indicator 198. The date indicator 198 in this example is shown as a dial, where only a small portion is visible through a window. This type of display mechanism is known in the art, and may be used for the date, state, or other aspect of the display. In this example, the state indicator 197 shows one of three states: sleep state (moon), normal activity monitoring state (sun), and activity counting (walking man). The activity counting state is used when the user is exercising, in one embodiment, to measure exercise intensity and provide exercise coaching. Other configurations may also be used.

Figure 2:
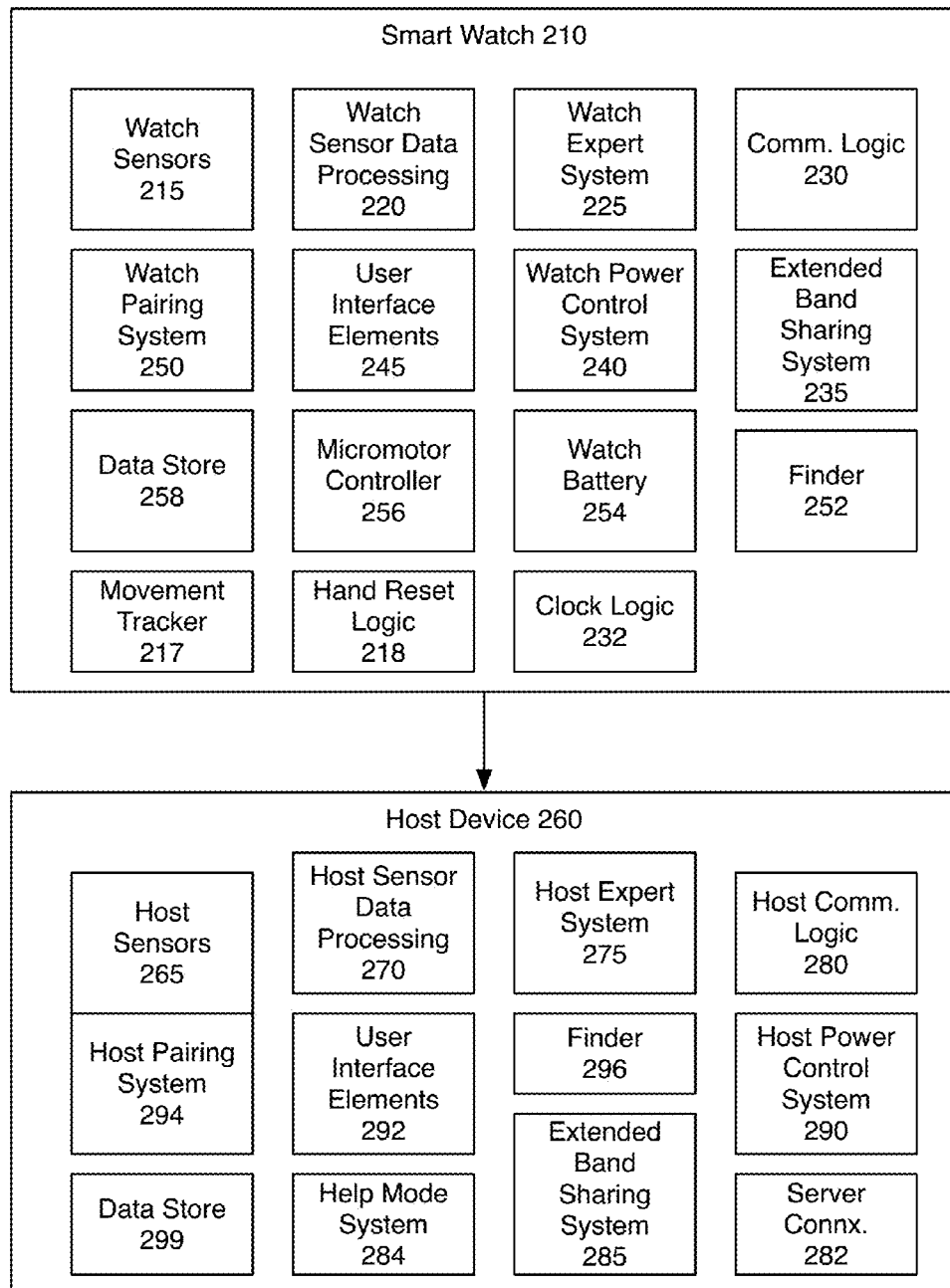
FIG. 2 is a block diagram of one embodiment of the extended band, including a smart watch and a mobile device working together.

FIG. 2 is a block diagram of one embodiment of the extended band, including a smart watch 210 and a host device 260 working together. Although only one smart watch 210 or band is shown, and one host device 260 is shown, it should be understood that multiple devices 210 may work together in various ways. In the below example, each logic is reproduced in both the smart watch 210 and the host device 260. In one embodiment, certain logics may be implemented in only one of the devices. If a logic or element exists in both devices, in one embodiment, the processing shared between the devices, and both devices can contribute data and processing power.

The smart watch 210 includes a plurality of sensors 215. The sensors, in one embodiment, may involve sensors used to detect the user's physiological condition. Such sensors may include an accelerometer, gyroscope, thermometer (potentially two thermometers, one for ambient and one for body temperature), barometer, etc. In one embodiment, additional sensors focused on medical applications may also be included. Such sensors may include blood glucose sensors, blood pressure sensors, blood oxygenation sensors, and other sensors. In one embodiment, the sensors may be coupled to the smart watch 210 or host device 260 wirelessly or using a wired connection.

The sensor data, obtained by sensors 215, is passed to band sensor data processing 220. In one embodiment, the sensor data processing 220 is implemented using a processor. In one embodiment, the sensors 215 may be coupled to a separate lower powered processor, and store the sensor data temporarily in a buffer (not shown). In one embodiment, the higher powered processor, which implements sensor data processing 220, may be turned on as needed. In one embodiment, the sensor data processing 220 may also be a low power processor, and any processing requiring higher power may use the host device 260. The host sensor data processing 270 may provide additional processing power.

Power control system 240 controls the processors and sensors of the smart watch device. In one embodiment, the smart watch 210 is powered by a watch battery 254, which is not rechargeable. The power control system 240 manages the sensor testing frequency, processing, and communication with host device 260 to reduce power consumption, and enable an extended battery life. In one embodiment, under normal use conditions, the watch battery 254 is designed to last up to two years, without replacement. In another embodiment, the watch battery 254 may be rechargeable using a plug-in or proximity charging technique. In one embodiment, by shifting out put from LEDs (light emitting diodes) to dials and hands controlled via micromotors, controlled by micromotor controller 256, the power consumption for the display is reduced.

One disadvantage of a micromotor controlled hand arrangement is that jarring can cause the hand to be misaligned compared to the actual time. In one embodiment, the smart watch 210 includes a movement tracker 217 which tracks the movements of the hands that are used to indicate the time. The tracker 217 tracks each motion of the hands, to enable comparison of the movement against the actual change in time. This enables the system to accurately adjust the hands of a horological clock, if they get misaligned due to accidental motion, jarring, or another reason Hand reset logic 218 is used to reset the hands to the proper location if they are jarred. As noted, the movement tracker 217 tracks the movement of the hands. Clock logic 232 obtains current accurate clock data, in one embodiment from host device 260. If the host device is a smart phone, the smart phone has a real-time clock source that is accurate in GPS or network clock data. This information is obtained by clock logic 232, and used to assist in correctly resetting the system.

Expert system 225 and host expert system 275 use the processed sensor data to make recommendations and analyze the results. The expert system is designed to utilize predictive analysis to predict the next actions, motions, stages of the user's activity, and to make recommendations.

Communication logic 230 in smart watch and host communication logic 280 enable the close tying of the smart watch 210 and host device 260. In one embodiment, communication logic 230 uses BLUETOOTH™ personal area network (PAN). Other network communication methods may be used. BLE (BLUETOOTH LOW ENERGY) also known as BLUETOOTH SMART may be the connection method. Other formats of network connection may be used. In one embodiment, data is sent in packets, so that the connection time for the transmission is minimized.

In one embodiment, the smart watch 210 may be physically coupled to the host device, continuously or periodically. The extended band sharing system on the smart watch 235 and host 285, work together to share processing and display. In one embodiment, the smart watch communication is limited by the user interface elements 245 available on the smart watch, such as a vibration motor and a limited number of subdials and/or LEDs, whereas in general, the host device 260 is a more fully featured, with a keyboard and screen.

User interface elements 245 on smart watch enable the user to interact with the watch. In one embodiment, the band user interface elements may include a button integrated into the watch crown, one or more subdials with associated hands, a vibration motor, and optionally one or more LEDs or a speaker or beeper. The user interface elements 245 on the smart watch in general are more limited than the user interface elements 292 in the host device 260. In one embodiment, the system is designed to provide basic communication to the user via the smart watch 210, and provide more details upon request via the host device 260.

Power control system 240 is used to minimize the power consumption by the smart watch 210. The power control system 240 reduces the power consumption of the smart watch, by shutting off sensors that are not being utilized, reducing sensor sample rates based on the current activity of the user, reducing band power consumption when the band is not being worn, and minimizing the use of the high power processing. In one embodiment, the power control system is a smart system, activating the subset of sensors and processing power required on an as-needed basis.

In one embodiment, data store on the band 258 may store sensor data from sensors 215, prior to processing. Post-processing data may also be stored in data store 258. In one embodiment, data store 258 may be a non-volatile memory, such as a flash memory. Data store 299, on host device 260 may be a non-volatile memory such as flash memory, or storage such as a disk drive. In one embodiment, the detailed long-term data is stored on a server (not shown), and sufficient data for display is stored on the host device 260. In one embodiment, the smart watch 210 only stores the data not yet sent to the host device 260, and data useful for the display, and calculations.

Pairing system 250 is used to initialize a connection between the smart watch 210 and the host device 260. In one embodiment, the pairing may use an automatic pairing, triggered by shaking the devices together or performing another activation mechanism. In one embodiment, the mechanism described in U.S. Pat. No. 7,907,901 is used.

In one embodiment, multiple smart watches and/or other body-worn devices 210 may be paired to a single host 260. This provides use flexibility and fashion. For example, an attractive horological wrist watch that is worn during a workday may be suboptimal for exercise or sleep. Therefore, different bands may have different functionality. Additionally, different bands may have different appearances. Additionally, in one embodiment, a single body-worn device 210 may be paired with multiple hosts 260. For example, a smart watch may be paired with the user's mobile phone, as well as the user's tablet computer, desktop, laptop, etc. Additionally a smart watch may be paired with a special purpose system.

In one embodiment, the system includes a help mode system 284, which enables a connection to 911 or other emergency numbers, as appropriate. In one embodiment, help mode system provides an interface that enables the user to securely, quickly, and unobtrusively invoke an emergency response from the smart watch 210, to trigger communication via host device 260. In one embodiment, multiple help modes may be available, depending on the emergency. For example, a fire may be a different help mode interface than a mugger or a medical emergency. In addition to being able to call 911 or the appropriate first responders, in on embodiment, help mode system 284 may also be set to contact a family member, doctor, or other appropriate party.

Finder 252 enables the user to find the host device via the smart watch, and vice versa. In one embodiment, the proximity system can alert the user when he or she leaves behind the smart watch 210, or the host device 260. This can be useful especially when the user puts down the host device 260, or takes off the smart watch 210 regularly. In this way, the extended band formed by the band 210 and host device 260 can provide an extended MACS (monitor, alert, control, share) system. The extended band provides functionality which neither the band 210 nor the host device 260 could provide alone. Additionally, by creating a truly linked band 210 and host 260, rather than occasionally sharing data, the extended band can take advantage of the combined feature set of both devices.

As noted the host device 260 can provide a different set of sensors 265, data processing 270, expert system 275, etc. The host device 260 has additional user interface features, including a full screen and keyboard. In one embodiment, the user can review his or her sleep pattern, activity pattern, and other health data on the host device 260 via user interface elements 292. Host device 260 also has a server connection 282, in one embodiment, which enables the host device 260 to provide data to the server. The server 282 in one embodiment stores user data from multiple users, and provides calculations for predictive algorithms, third party data, and updates. Though only a single server is mentioned, it should be clear that the system may connect to multiple servers. For example, a first server may provide the application for the host device 260, and updates to the application, while a second server may be a data store for user data, and a third server may provide third party data, and other information.

Figure 3A:
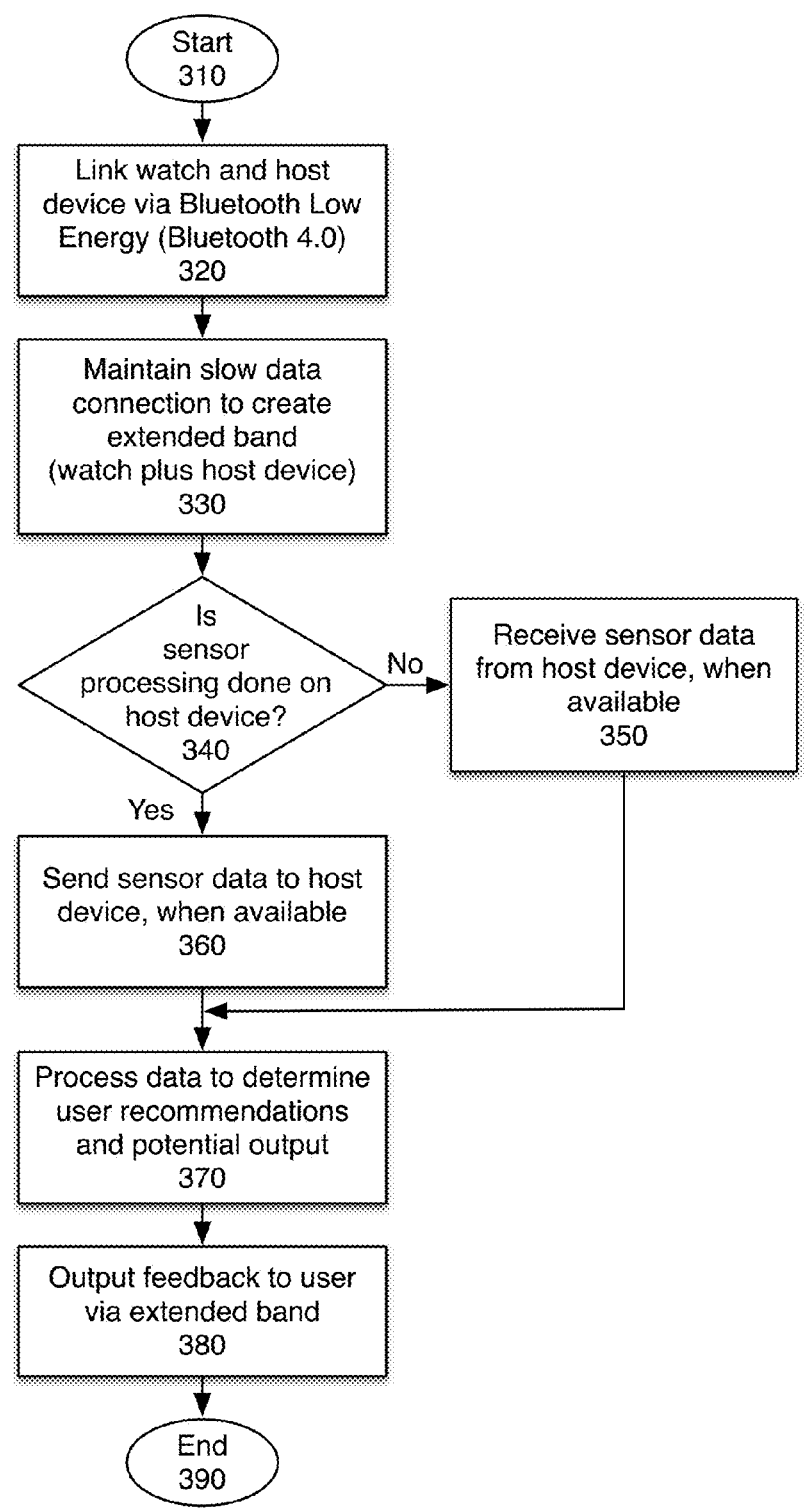
FIG. 3A is an overview flowchart of one embodiment of using the extended band.

FIG. 3A is an overview flowchart of one embodiment of using the extended band. FIG. 3A illustrates using a Bluetooth Low Energy (BLE, also known as Bluetooth 4.0) connection. Of course, other embodiments may use other wireless protocols. By preference, in one embodiment, low power wireless protocol is used. The process starts at block 310, when the smart watch is initially activated.

At block 320, the smart watch and the host devices are paired via the low-power wireless protocol. In one embodiment, that protocol may be the BLE protocol. In one embodiment, pairing is done as described in in FIG. 4 below.

At block 330, a slow and low-power data connection is maintained between the smart watch and the host device, to create the extended band. The extended band is a combination of the sensors, processors, input and output mechanisms of the smart watch and the host device. The combination can provide better quality data, faster processing, and a richer output than either device alone.

At block 340, the process determines whether sensor data processing is done by the host device, the smart watch, or a combination. In one embodiment, if both the host device and the smart watch can do processing, the processing will be distributed as is most efficient. In one embodiment, the decision may be made based on processor capability, available battery power, bandwidth cost, and sensor data volume. In one embodiment, the host device has a more powerful processor but the smart watch has more sensors. In one embodiment, pre-processed sensor data is shared, rather than raw data.

The process determines whether the processing is being done on the host device, at block 340. If the processing is not done on the host device, at block 350, in one embodiment, sensor data is received by the smart watch from the host device. If the processing is done on the host device, at block 360, sensor data is sent to the host device by the smart watch. In one embodiment, each device may do some preprocessing on its sensor data, before sharing it. Preprocessing data removes unnecessary data. For example, for a motion sensor, the accelerometer output is a change in acceleration at all times. The pre-processed data may remove portions that contain no movement. In one embodiment, the pre-processed data, for an accelerometer, may provide an acceleration vector showing direction, strength, and length of movement, rather than raw accelerometer data. In one embodiment, each device may process its sensor data separately.

At block 370, the data is processed to determine user recommendations and outputs. In one embodiment, the outputs may be alarms, reminders, status indicators, status updates updates, etc. In one embodiment, feedback is output to the user at block 380. The feedback may additionally be shared on social networks, or pushed to other users of the application, in one embodiment. The process ends at block 390. In one embodiment, the connection is maintained when the devices are both powered and available, and thus this process ends only when one of the two devices is disconnected or turned off.

Figure 3B:
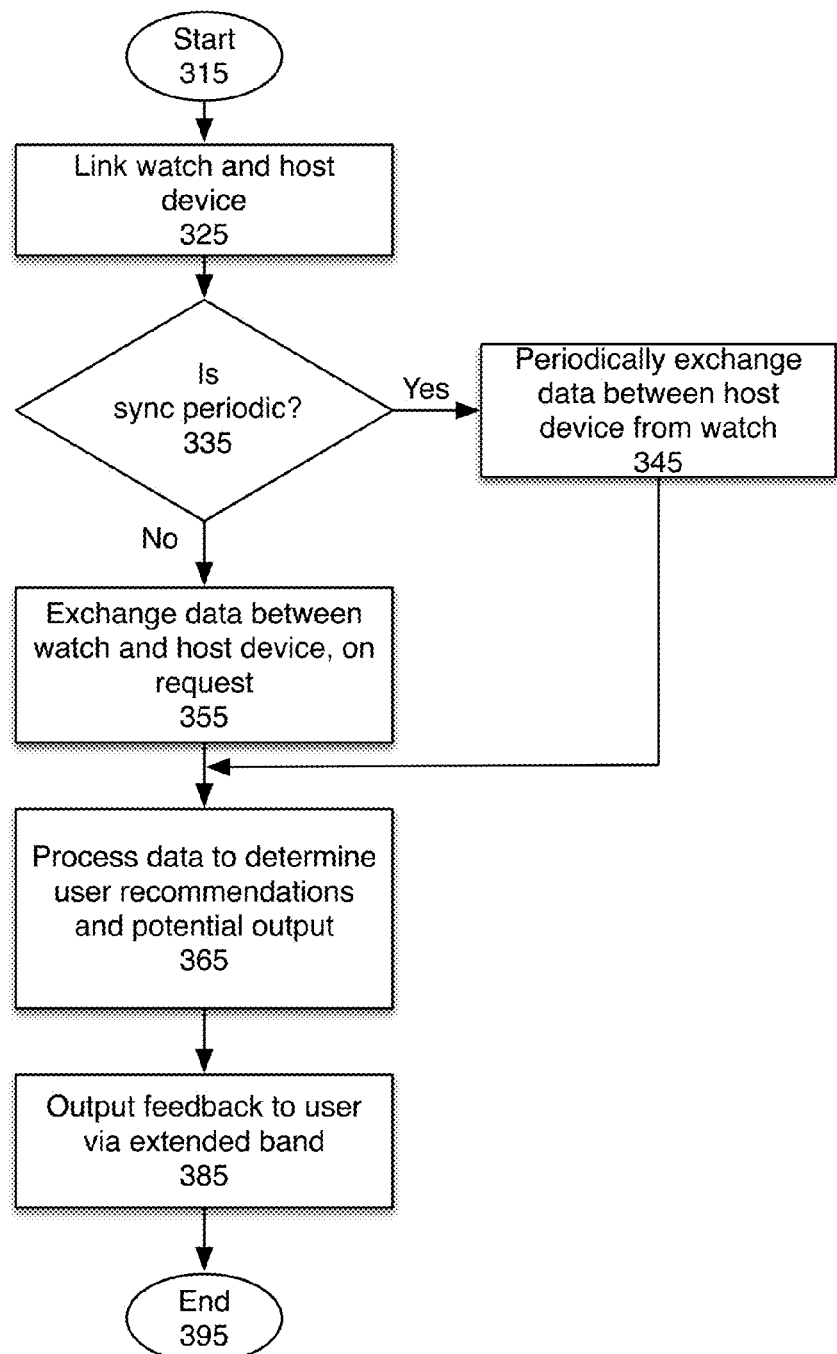
FIG. 3B is an overview flowchart of another embodiment of using the extended band.

FIG. 3B is an overview flowchart of another embodiment of using the extended band. The process starts at block 315, when the smart watch and host device are initially associated.

Figure 4:
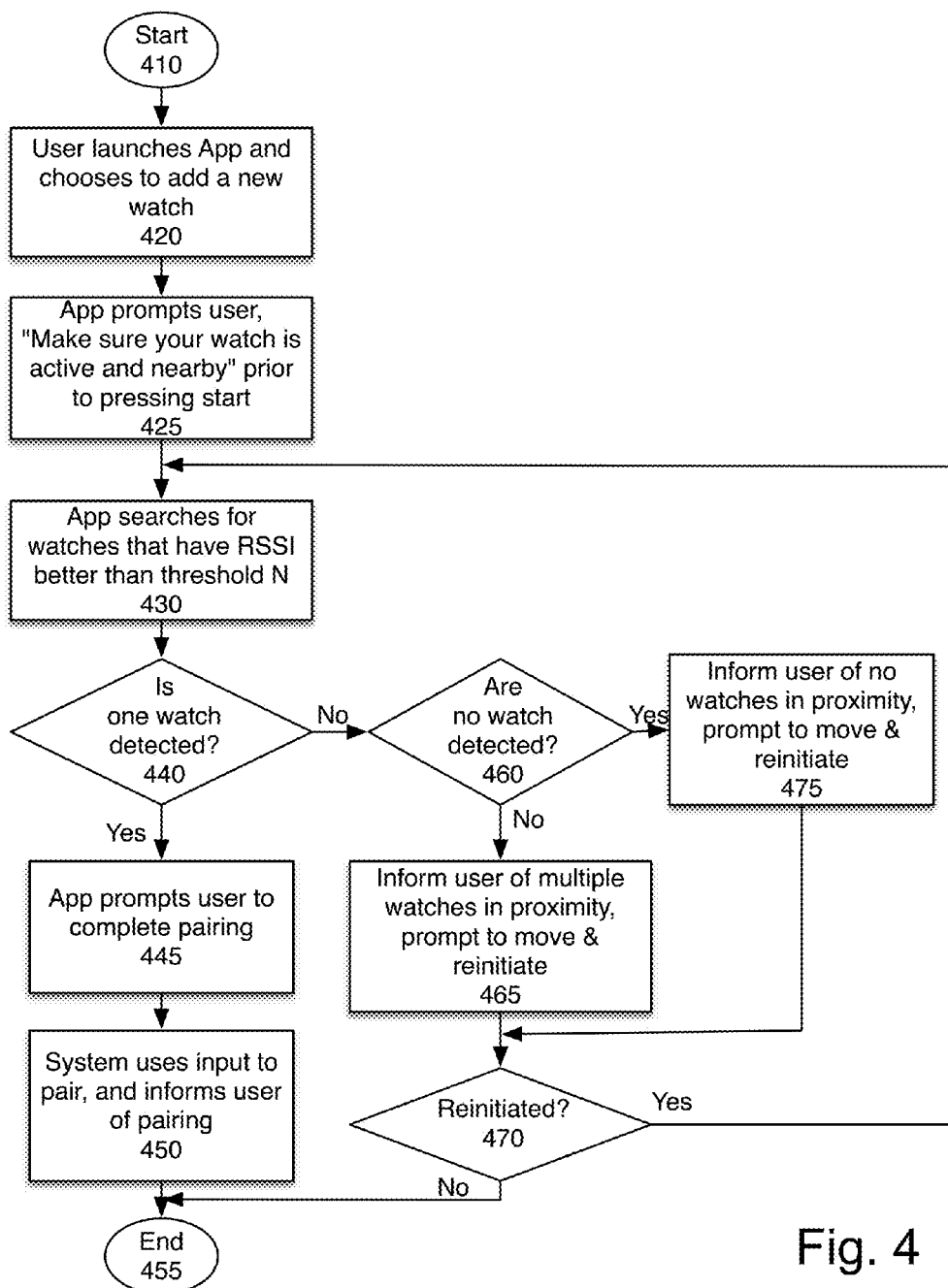
FIG. 4 is a flowchart of one embodiment of pairing the mobile device and the smart watch.

At block 325, the watch and host device are linked. In one embodiment, the pairing method described below with respect to FIG. 4 is used. In one embodiment, the host device has the ability to "ping" when in pairing mode, and connect to any available smart watch. Other methods of pairing or associating the devices may also be used.

At block 335, the process determines whether the sync is periodic. A periodic sync means that the data is shared between the watch and the host device periodically. The period may be defined in various ways. In one embodiment, the period may be defined by time, e.g. every five minutes, by data accumulation, e.g. after X amount of data is collected, by processor usage, e.g. when the watch processor is otherwise idle, by need, e.g. when the watch is in need of additional sensor data or processing capability, or a combination of these or other period definitions. In one embodiment, the host device may also initiate the periodic synchronization. If the sync is periodic, at block 345, the system periodically exchanges data between the host device and the smart watch. The process then continues to block 365.

If the sync is not periodic, the process continues to block 355. At block 355, data is exchanged between the smart watch and host device on request. The request may be a manual request from the user. The request may be an automatically generated request from the host device, or from the watch. For example, the host device may automatically request data if the user activates the application and no recent data has been received. For example, the watch may request data when the user places the watch into sleep state, and there is no alarm setting data available on the watch, or the alarm setting data has not been validated recently. In one embodiment, the on-request data exchange may be a full data exchange, or a limited data exchange as needed to service the user's needs. The process then continues to block 365.

At block 365, the data is processed, to determine user recommendations and potential output. In one embodiment, the data processing includes predictive modeling of the user's expected activity/sleep pattern, and comparison of actual sensor data against the predictive modeling. This enables the system to adjust the sensor and data processing frequency to match the expected actions, and to identify the actual actions more quickly and with less processing. The recommendations for the user may range from engaging in an activity, e.g. inactivity alarm, to coaching, e.g. providing guidance during an exercise session, to suggestions.

At block 385, feedback is provided to the user, if appropriate, via the extended band. As noted above, feedback via the smart watch may include data displayed on a dial, or via LEDs, vibration, or alarm tones. Data displayed via the host device may be more detailed. In one embodiment, the feedback may be provided via alternative means, such as an email, SMS, or social media post.

The process ends at block 395. In one embodiment, the connection is maintained when the devices are both powered and available, and thus this process ends only when one of the two devices is disconnected or turned off.

FIG. 4 is a flowchart of one embodiment of pairing the mobile device and the smart watch. This describes the initial pairing of a new watch to a host device. In one embodiment, this flowchart corresponds to block 320 of FIG. 3. The host device runs an application (app), which is used to provide input/output for the extended band. The process starts at block 410.

At block 420, the user launches the application, and chooses the option to add a new smart watch. In one embodiment, this may be done from a configuration menu or the like in the application. In one embodiment, this may be done using a hardware button or similar mechanism.

At block 425, the application prompts the user to make sure the smart watch is active and nearby, prior to pressing start. The start button may be a soft button or a hard button. In another embodiment, the start button may be a gesture command or other initiation mechanism.

At block 430, the application searches for a smart watch that has a received signal strength indicator (RSSI) greater than a threshold.

At block 440, the process determines whether a single watch is detected. If so, at block 445, the application prompts the user to complete the pairing. In one embodiment, this is done by performing a gesture command to complete the pairing. This ensures that the watch whose signature was detected is the band being paired. The gesture command, in one embodiment, is holding the host device and the watch together and performing a motion. In another embodiment, button press or other interaction with the watch may be used instead to complete the pairing. In another embodiment, the watch ID (which may be the brand name, or another identification) is displayed and the user can accept the pairing. In one embodiment, the user may need to accept the pairing on both the watch and the host device, to ensure that an unrelated host device can't be paired with a watch.

At block 450, the input is used to pair the host device and band. In one embodiment, the process described in U.S. Pat. No. 7,907,901, assigned to the assignee of the present invention, may be used to perform the pairing. The user is informed of the pairing. The process then ends at block 455.

If at block 440 the system did not detect a single watch, the process continued to block 460. At block 460, the process determines whether no watches were detected. If no watches were detected at block 475 the user is informed that no watches were successfully detected, and the user is prompted to ensure that the watch to be paired is active and in proximity to the host device. The process then continues to block 470, enabling the user to reinitiate the pairing. If the user reinitiates the pairing, the process returns to block 430, to search for watches in proximity with an RSSI above a threshold. If the pairing is not reinitiated, the process ends.

If, at block 460 multiple watches and/or bands were found, in one embodiment, the process continues to block 465. At block 465 the user is warned that multiple devices were found in proximity, and prompted to move, with the one watch to pair and the host device, or alternatively to remove the other devices from the vicinity, or turn them off. The process then continues to block 470, enabling the user to reinitiate the pairing. In another embodiment, the user may simultaneously pair multiple watches or other devices with the host device. In that case, the process continues to block 445 when the one or more watches are detected, and the user accepts the pairing with each device.

In this way, the system enables establishing the pairing between the host device and the watch. Once a host device and a watch are paired, forming the extended band, whenever the two devices are in proximity they can automatically establish a connection. Additionally, as described above, the extended band utilizes the combined sensor set and processing power of the watch and the host device.

Figure 5:
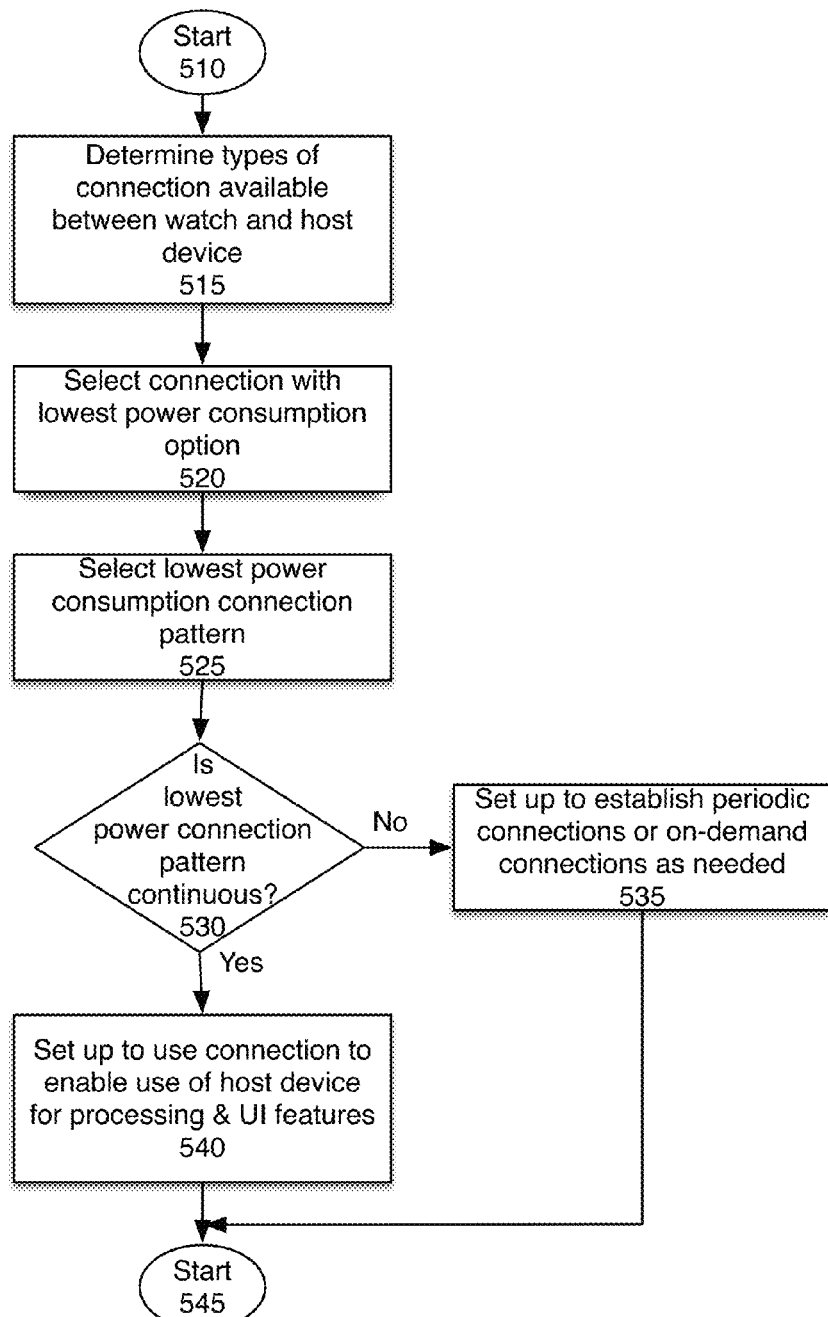
FIG. 5 is a flowchart of one embodiment of selecting a connection method between the mobile device and the band.

FIG. 5 is a flowchart of one embodiment of selecting a connection method between the host device and the watch. In one embodiment, watches may be connected to various host devices such as a smartphones, special purpose mobile devices, tablet computers, mini tablets, laptop computers, desktop computers, or other devices. These various host devices may have different capabilities, in terms of types of wireless connectivity. The types of wireless connectivity may include various types of wireless personal area networks (WPAN), local area networks (LAN), 802.11-type networks, and other types of connections.

At block 515, the types of connections available between the watch and host devices are identified. The types of connections include all connection formats that are supported by both the host device and the watch.

At block 520, the lowest power connection that can support the data exchange between the watch and host device is selected. Because the watch is designed to monitor motion, sleep, and ergonomics, it is designed to be worn continuously. Therefore, long battery life is strongly preferred, and minimizing power consumption is an important goal.

At block 525, a connection pattern that is the lowest consumption is selected. Depending on the type of connection, the lowest consumption pattern may be a continuous connection sending small amounts of data (Bluetooth 4.0) or periodic connections to send high bandwidth bursts of data. In one embodiment, based on the connection method selected, the lowest power connection pattern is selected.

At block 530, the process determines whether the selected connection pattern is continuous. As noted above, for some connection formats, a continuous low power connection is preferred. If so, at block 540, the system is set up to use a continuous connection, at block 540. In one embodiment, the continuous connection exchanges data in a low bandwidth format regularly. If not, at block 535 the system sets up timing for periodic connections, or sets up a pattern of establishing connections as needed. The process then ends.

Figure 6:
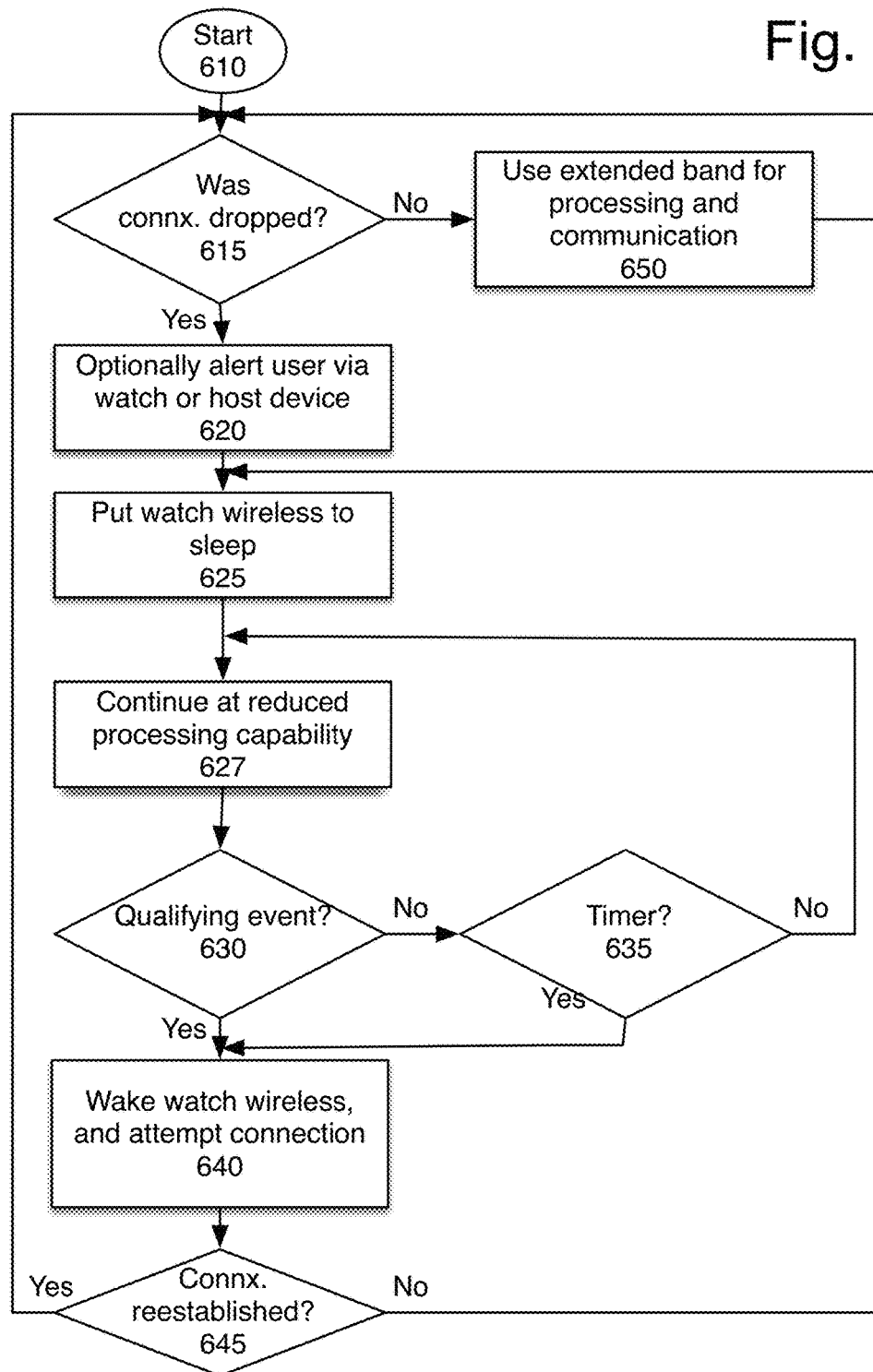
FIG. 6 is a flowchart of one embodiment of handling lost connections in the extended band.

FIG. 6 is a flowchart of one embodiment of handling lost connections in the extended band. In one embodiment, the extended band assumes that that connection between the watch and the host device is on-going, either continuously or on a periodic basis. When the systems cannot connect, in one embodiment, the following process is used. The process starts at block 610. In one embodiment, this process is continuously or periodically validating the connection.

At block 615, the process determines whether the connection was dropped. A dropped connection occurs if an attempt to share data between the watch and the host device fails. In one embodiment, at least a plurality of attempts must fail, to declare a connection dropped. In one embodiment, if three attempts fail, the connection is deemed dropped.

If the connection has not dropped, at block 650 the combination of watch and host device is used to acquire sensor data, process it, and communicate with the user. Additionally the extended band may share data with third parties including social networks, as well as present data to the user, in one embodiment including from third parties including social networks. The process continues back to block 615, to continue utilizing the extended band and monitoring for a dropped connection.

If the connection was dropped, at block 620 the user is alerted via the watch and/or host device, in one embodiment. The alert may be useful to indicate that the watch or host device was left behind accidentally, has been turned off, or has developed a problem. In one embodiment, the alert on the watch may be a vibration or light, while the host device may use an alarm tone and a display on its screen. Other methods of alerting the user may be used. In one embodiment, a text or MMS message may be generated to alert the user.

At block 625 the watch wireless connection is put to sleep. As noted above, the watch power use should be minimized. Wireless connectivity is one of the significant battery drains, and especially unsuccessful attempts to connect wirelessly uses a lot of signal strength and thus battery. Therefore, temporarily placing the watch's wireless connection in a sleep state is a way of preserving battery power.

At block 627, the other processes of the watch are continued, at a reduced level. In one embodiment, if the watch cannot process some of the sensor data, it stores and queues the data to be sent to the host device. From the user's perspective, in one embodiment, the watch functionality does not significantly change, unless the watch cannot support the required processing. In that case, the system attempts to continue functioning with the reduced processing power, prioritizing user-relevant actions. For example, if the user is sleeping and awaiting an alarm, the watch would continue to monitor sleep and ensure that the alarm was not missed. Other processes may be queued for later processing. The watch also queues other communications that would normally take place with the host device, e.g. user status updates and processed sensor data.

At block 630, the process determines whether a qualifying event has taken place. A qualifying event may include the user pressing a button on the band, ending a sleep or timed steps recording, the watch detecting that it is time to wake-up the user (smart sleep alarm), etc. In one embodiment, a qualifying event is any event that should lead to communication between the host device and the watch. If a qualifying event is detected, at block 640 the watch wireless connection is woken, and the watch attempts to connect to the host device again. At block 645, the process determines whether the connection was reestablished. If not, the process continues to block 625, and puts the wireless connection back to sleep. Of course, the watch would also perform the actions triggered by the qualifying event. If the connection is successfully reestablished, the watch sends the data previously queued to the host device, and the process returns to block 615 to continue interacting with the host device and monitor the status of the connection.

If no qualifying event took place, at block 630, at block 635 the process determines if a timer has triggered. If the time set by the timer has not passed, the process returns to block 627, to continue reduced service, and determine whether a qualifying event has been detected. If the timer has been triggered, at block 640 the watch wireless is woken, and a connection is attempted.

In this way, the almost continuous connection between the watch and the host device is maintained, while optimizing for reduced power consumption by the watch and user-relevant processing when processing is limited to the watch. Although this figure shows the dropped connection from the perspective of the watch, one of skill in the art would understand that the host device can use a similar process. When the sensor data, and other information from the watch is not available, the host device continues to process what data it has available, and attempts to keep the user experience consistent. In one embodiment, if the system is being used for sleep monitoring, the host device may change to a user-modified sleep pattern, and still wake the user using a smart alarm. This is designed to ensure that if the watch runs out of power, or crashes, or otherwise becomes inactive, the user still has a positive experience with the system.

FIG. 7 is a flowchart of one embodiment of using the extended band. The process starts at block 710. At block 715, the process determines whether the watch is above a motion threshold. This determination attempts to identify whether the watch is being worn, or not. Even when not moving a human body exhibits certain motions, such as tremors and a rhythmic movement caused by the heart beating. The motion threshold is set, in one embodiment, to be able to use these involuntary motions to determine that the watch is in use.

If the watch is below the motion threshold, at block 720 the process determines whether the watch has been inactive for a period of time. If so, at block 725, the sensors in the watch are powered off, or placed on a low testing frequency. The process then ends at block 730. In one embodiment, the watch sets a timer, and periodically checks if there is movement above a threshold. In another embodiment, at least one sensor is maintained at a low rate, to continue monitoring. The sensor may be the temperature sensor, accelerometer, or other low power sensor that is capable of detecting either motion or temperature or another identifier that would indicate that the watch is being worn. In another embodiment, the user manually activates the sensors in the watch after they are powered off. In one embodiment, a dial may set the watch to a setting indicating that the sensors are off.

If the watch has not been inactive for a period, the process returns to block 715, to continue monitoring whether the watch motion level is above the threshold.

If the watch motion is above the threshold, as determined at block 715, the process continues to block 740. At block 740, the process determines whether host device finder was initiated on the watch. In one embodiment, when the user is wearing the watch and cannot find his or her host device, which is a mobile device, he or she may activate this feature. If it was activated, at block 745 a message is sent to trigger an action on the host device. In one embodiment, the message is sent through the application that may be able to override a silent setting. This enables the user to locate the host device, if the host device has any power. In one embodiment, the output is played repeatedly until the user indicates that the host device has been found. In one embodiment, if the watch and host device are not in close enough proximity to use the personal area network such as BLUETOOTH, another network protocol may be used for this message. The process then returns to block 715.

If the host device finder is not activated, the process determines whether the watch device finder on the host device is activated, at block 750. If so, at block 755, a message to use the watch output is sent from the host device to the watch. The output may be a sound, a vibration, a flashing light, or a combination of those or any other forms of output that the watch can utilize. In one embodiment, the output is played repeatedly until the user indicates that the watch is found. In one embodiment, if the watch and host device are not in close enough proximity to use the personal area network such as BLUETOOTH, another network protocol may be used for this message. In one embodiment, if the host device has the capability to determine the location of the watch, the system may also provide an indication of the location or approximate direction of the band. The process then returns to block 715.

If the watch finder was not initiated, at block 760, the process determines whether a help mode is initiated. The help mode may be initiated by pressing and holding a button, or another indication on the watch. In one embodiment, this indication is designed to not be accidentally triggered, and easy enough to enable someone who is hurt to perform the indication.

In one embodiment, the user may utilize the watch to initiate a help mode. The help mode connects the user to an emergency number, such as 911 or a pre-programmed third party such as a doctor or monitoring service, using a combination of the watch and the host device. This would enable a user who is unable to reach or dial a telephone to call for help.

If the help mode is initiated, at block 765, the system uses the extended band to connect to the emergency line. In one embodiment, the combination of the host device and the watch enables a user to talk to the emergency number responder (such as a dispatcher) without having to dial and hold a telephone. In one embodiment, there may be multiple types of help modes that may be triggered. For example, there may be a "medical emergency" trigger, a "non-medical emergency" trigger, and a "dangerous situation" trigger. In one embodiment, the user may define one or more triggers, and one or more destinations. In one embodiment, the default help mode initiation is to contact 911 or the equivalent local emergency service.

In one embodiment, help mode may be initiated automatically, e.g. without a user triggering it, in some circumstances. For example, in one embodiment, if the watch sensors detect that the user is having a medical emergency, help mode may be initiated. For example, if the watch can monitor heart rate automatically, a heart rate in the danger zone (e.g. heart arrhythmia or heart racing without a corresponding movement trigger) may automatically trigger the help mode. In one embodiment, the user is provided with the opportunity to override the help mode trigger, if it is automatically initiated. In one embodiment, the ability to terminate the help mode is also provided when it is manually triggered, enabling the user to override it. The process then returns to block 715 to continue monitoring.

If no help mode was initiated, the process at block 770 determines whether the system has received data from other users. In one embodiment, the user may set up one or more "friends" with whom the user wishes to share data, and whose data the user wishes to see. If one of those friends has sent data, at block 775 the data is received and shared with the user. In one embodiment, the system includes a page that displays the user's own status and the status of friends. The data received may include social media posts, such as posts on FACEBOOK®, or TWITTER® or another social media platform. The data received may include data directly shared between instances of the application, e.g. each user may set up to share certain milestones achieved, such as how much and how well the user slept, how much aerobic activity the user did, how many steps the user took, etc. In one embodiment, the received data is a combination of these types of data. In one embodiment, the user may be alerted to certain social media data, based on user-set preferences. The process then returns to block 715 to continue monitoring.

If no data is received, at block 780, the system provides normal user status to the user throughout the day. The user interface on the watch is updated throughout the day, as is the user interface available via an application on the host device so that it is up-to-date with the user's latest activity and/or sleep data. It is designed so that the user can glance at the watch and see how he or she is doing today. In one embodiment, by incorporating the shared data received from others, the user can also see one the host device how he or she is doing relative to personal activity/sleep goals and relative to other people/friends in their social network.

In one embodiment, the watch also provides some of this feedback throughout the day. In one embodiment, the watch has subdial which provides progress information, using a dial and hand, which allows for feedback/status updates throughout the day. In one embodiment, the user's current status may be reflected by an LED or other illustrating showing a relative status (e.g. green when the user has met his or her goals, shading into yellow as they slip, and red when the user is far from his or her set goals). Alternatively, the user's relative standing among his or her friends may be indicated via display on the watch. For example, there may be a dial indicating user status, with the dial pointing to a gold, silver, bronze, or other level, depending on the user's relative placement. In one embodiment, LEDs with various colors may be used. This enables an at-a-glance comparison between friends. In one embodiment, a competition logic, described for example in U.S. patent application Ser. No. 11/740,884, assigned to the assignee of this case, may be used to enable competition between unevenly matched users.

In one embodiment, in addition to providing data to the user, the process also enables the user to selectively share the user's status with friends. As noted above, the application may share certain achievements and status. In one embodiment, the user sets up what information is shared with whom, and once the preferences are set, the extended band automatically shares data. In one embodiment, the user may also manually share data, or block data from being shared. The process then returns to block 715 to continue monitoring.

In this way, the extended band, utilizing the watch and the paired host device provide services to the user. Additional services may be provided, with sensor data, sensor data processing, data sharing, and notifications utilizing the watch, the host device, or both devices. By providing an extended band that is linked consistently with the host device, the user has the advantages of both form factors, and the disadvantages of neither.

FIG. 8 is a flowchart of one embodiment of optimizing the sharing or processing and display on the extended band. The process starts at block 810. In one embodiment, this process is continuous when the extended band is in use.

At block 815, the process determines whether there is user output to be provided. The system provides alerts, alarms, and other types of notifications to the user. In one embodiment, this does not include updates to the user's information presented on the watch or host device, as discussed with respect to FIG. 7.

If there is user output to be provided, the system at block 820 identifies the optimal combination of outputs based on the type of connection between the host and band, power levels of the host and band, and host and band capabilities. In one embodiment, the system preferentially outputs user alerts through the watch, and more detailed data through the host device, since the host device provides a richer experience. In one embodiment, the relative location of the host device and watch may also be taken into account, e.g. if the user is wearing the watch but the host device is not nearby, the watch may be a better output mechanism. In one embodiment, the distance between the host and watch may be determined based on connection latency. In one embodiment, if one of the devices has low power, the system preferentially uses the other device in the extended band to provide feedback to the user. FIG. 9 illustrates some exemplary methods of providing output to the user. In one embodiment, the watch includes one or more subdials, and a vibration engine, to provide information to the user. In one embodiment, the hands on the subdials are moved via micro-motors. Any of the exemplary interface methods discussed in FIG. 9 may be altered, of course, without deviating from the present invention. Once the optimal combination of the outputs is determined, at block 825 the output is provided to the user. The process then returns to block 815 to continue monitoring.

If there is no output to be provided, the process determines whether there is data to be processed. The data to be processed may include sensor data such as motion data, heart rate data, or other types of data. The data to be processed may also include third party data. In one embodiment, data processing includes not only using raw sensor data to determine the user's activities, sleep phase, ergonomics, etc., but also providing trend analysis and other processing. If there is data to be processed, at block 835 the process identifies the ideal combination of the watch and host device, and optionally a remote system such as a server, to process the data. In one embodiment, this too may be based on the capabilities, power levels, and data sets available to the devices. The process at block 840 then determines whether the data needs to be passed from its current source for processing. If not, the processing takes place and the process returns to block 815 to continue monitoring.

If at block 840 the process determines that the data needs to be passed, at block 845 the data is passed from the watch to the host device/server, or from the host device to the watch/server, or in some other configuration, as determined. The data is then processed. In one embodiment, if the other device will use the data, in one embodiment the processed data, and/or the conclusion that results from the processing, is passed back at block 850. In another embodiment, the result of the processing is passed back. In one embodiment, a relevant output or change in settings or state based on the data is passed back. In another embodiment, no data is returned. The process then returns to block 815 to continue monitoring.

If there is no data to be processed, at block 855 the process determines whether there is sensor data to be shared. If so, at block 860 the sensor data is received. The sensor data may be received by the watch from the host device, or by the host device from the watch. The process then returns to block 815 to continue monitoring.

If there is no sensor data to be shared, the process continues to block 865. At block 865, the process determines whether the watch or host device is low on power. If a watch or host device is low on power, in one embodiment, the system attempts to reduce the likelihood that it will run out of power entirely, by reducing the demands made by the extended band on the low-battery device.

If a device is low on power, at block 875 the processing and output is shifted to the other device. At block 880, the inessential elements of the device are turned off. For example, if the watch is low on power, in one embodiment, all sensors except the motion sensor may be turned off. In one embodiment, if the host device has an available motion sensor and is being carried, the motion sensor may also be turned off. In normal use, when power levels are not an issue, the host device and the watch may both monitor user motions, to provide a more detailed picture of the user's activities. However, when a power issue comes up, the elements not absolutely necessary may be turned off, to extended battery power. If there is no power issue, the process continues directly to block 815. In one embodiment, the system may minimize power consumption even when there is not a low power issue. In that case, in one embodiment, only one carried device would monitor movement and other physiological data, and only one device outputs information to the user. This is less accurate than having two sets of data, but is more power efficient. In one embodiment, the trade-off level may be set by the user. The process then returns to block 815, to continue monitoring the user.

Figure 10:
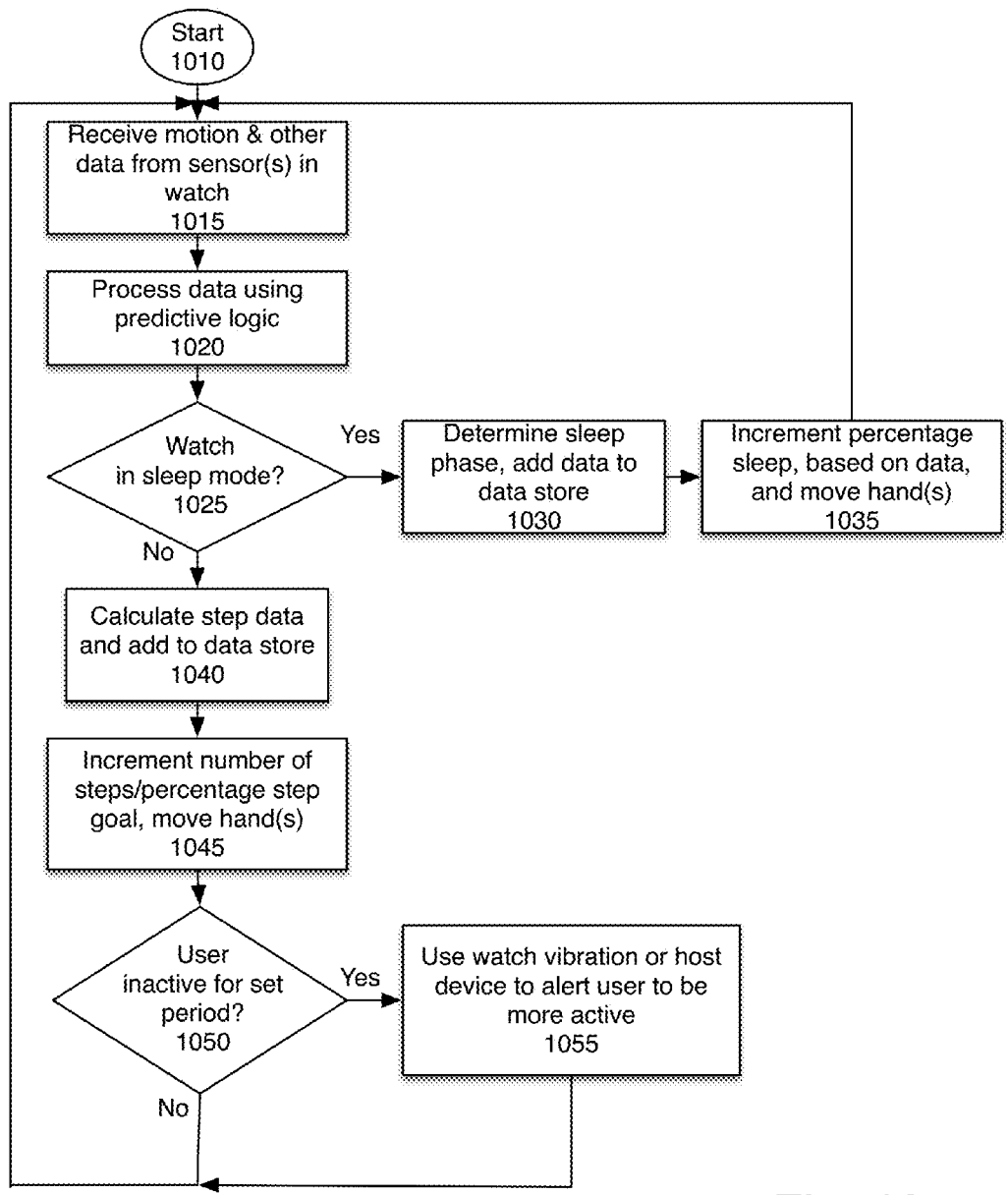
FIG. 10 is a flowchart of one embodiment of showing data on the smart watch using the horological display.

FIG. 10 is a flowchart of one embodiment of showing data on the smart watch using the horological display. The process starts at block 1010. In one embodiment, this process is active whenever the smart watch is active.

At block 1015, the system receives motion and other available data from sensors in the watch. In one embodiment, the sensors may include temperature, acceleration/gyroscope or other motion sensors, magnetic sensors, barometers, heart rate sensors, etc. In one embodiment, data may also be received from sensors in the host device, or external sensors.

At block 1020, the data is processed using predictive logic. Predictive logic utilizes the existing information about the user and the patterns of behavior to predict future behavior. This allows the system to compare the actual data to the predicted data, and confirm or disprove the expected behavior. This enables analysis of behavior based on less data, and with less processing.

At block 1025, the process determines whether the watch is in sleep state. If so, at block 1030, the sleep phase is determined. The sleep phase is predicted based on the past sleep states, the time, and the sleep cycles of the user. The sleep phase is verified using the sensor data. Once the actual sleep state is identified, the data is added to the data store. At block 1035, in one embodiment, the percentage of sleep, compared to the sleep goal is incremented. The hands are moved on the dial, to visually represent the percentage sleep achieved, compared to the set sleep goal. In one embodiment, the display may represent not only an overall sleep goal, but also a sleep goal by sleep phase (e.g. hours in each sleep phase, N1, N2, N3, and REM sleep, or deep sleep & REM sleep.) In one embodiment, this type of additional data may also be represented on the watch. The process then returns to block 1015, to continue monitoring the user.

If the watch is not in sleep state, the process continues to block 1040. At block 1040, step data is calculated for the user and added to the data store. Again, in one embodiment, the predictive logic makes a base assumption, for example, if the user is walking and not at a known end location, the user will keep walking. The sensor data is used to validate the assumption. The result is added to the data store.

At block 1045, the number of steps or percentage of steps to the step goal is incremented, and the hands of the watch are moved to represent the current results. In one embodiment, in addition to measuring a step goal, the system may alternatively or additional measure vigorous exercise, overall activity, and other measurements.

At block 1050, the process determines whether the user has been inactive for a set period. In one embodiment, the user may configure the watch to alert him or her after a certain period of inactivity. For example, the watch may buzz or chime after the user has been inactive for at least 30 minutes. This period, and the presence of this alert, may be configured by the user, on the host device.

If the user has been inactive, at block 1055, the user is alerted to move. In one embodiment, the alert may be a vibration or tone on the watch, or a more detailed alert on the host device. In one embodiment, the user may be prompted, on the host device, to stretch or otherwise become active for a short period. It is unhealthy to be sitting still for extended periods, and by sending such alerts, the user's overall wellbeing is improved. The process then returns to block 1015, to continue monitoring the user. If the user has not been inactive, the process returns to block 1015 directly, to continue monitoring the user.

Figure 11:
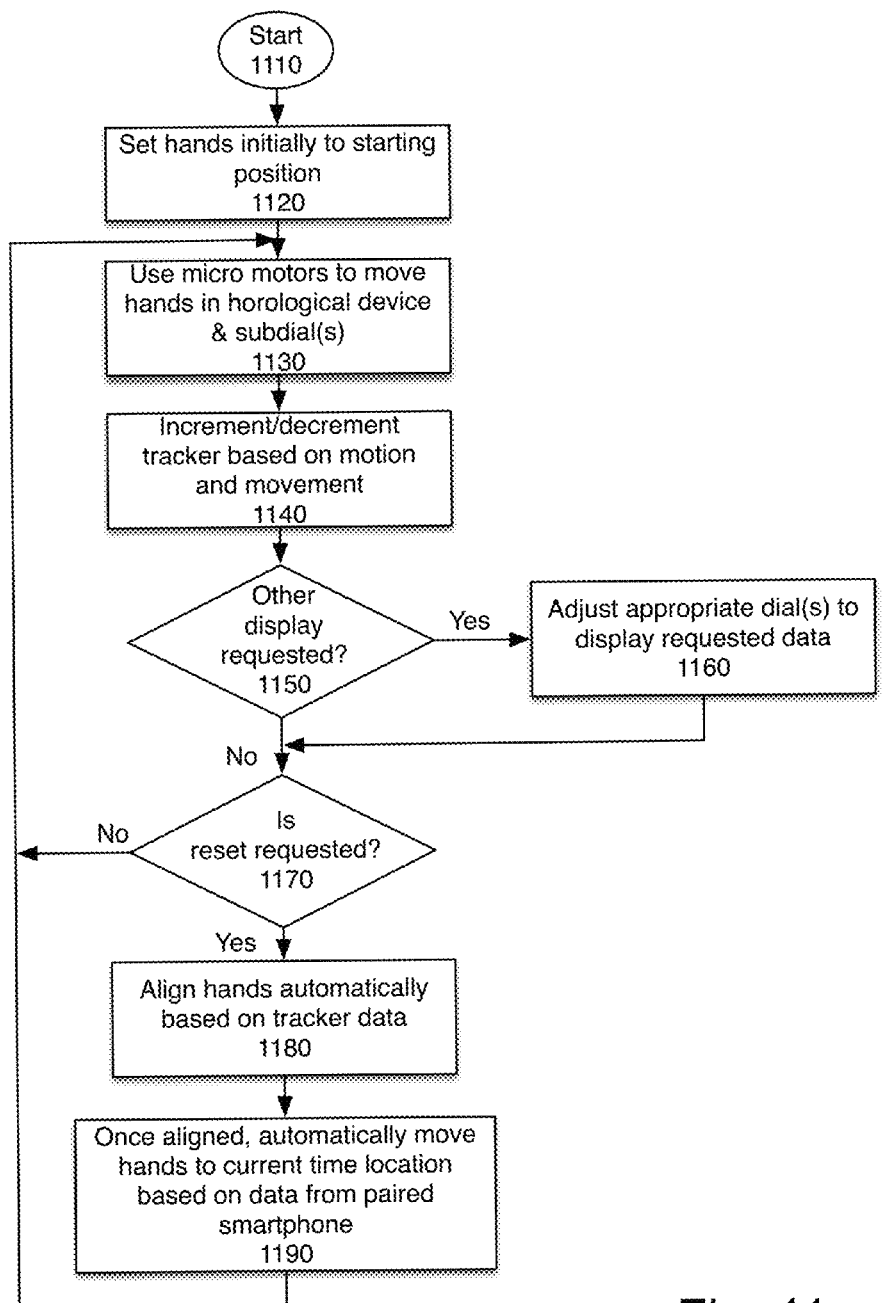
FIG. 11 is a flowchart of one embodiment of resetting the hands on the watch, in accordance with the present system.

FIG. 11 is a flowchart of one embodiment of resetting the hands on the watch, in accordance with the present system. The process starts at block 1110. This process in one embodiment is started when the smart watch is initially configured.

At block 1120, the hands of the smart watch are set to the initial starting position. This is needed for the system to be properly initialized. This may be done at the time of assembly or initialization.

At block 1130, the micromotors are used to move the hands in the horological device, one or more subdials. The subdials may present information about the user's activity, sleep, or other aspect monitored by the smart watch. Dials may include hands, pointing to a number or symbol, or a window displaying a number or symbol, such as a date window. The horological dial shows the current time, and optionally day. Other aspects that may be displayed via subdials may be a state indicator, indicating smart watch state (e.g. awake, sleeping, and active), the percent or total steps taken or sleep achieved, etc.

At block 1140, a tracker is adjusted, based on the motion and the movement. The tracker tracks the movements of the hands, whether those movements are caused by the micromotors (e.g. actual changes) or by jarring or other issues.

At block 1150, the process determines whether another display is requested. In one embodiment, the hands may have multiple output functions, for example time and health status, or date and step goal percentage, etc. If another display is requested, at block 1160 the appropriate dial(s) are adjusted for the requested data. The tracker, in one embodiment, continues tracking all changes to the display. The process then continues o block 1170.

At block 1170, the process determines whether a reset of the hands is requested or needed. A reset is requested when the user wants to adjust the hands, either to reset from a different display, or because the user has noticed a discrepancy between the display and the actual time. The system may automatically detect that a reset is needed, at block 1170, when the location of the hands, based on the tracker data, does not correspond to the actual location of the hands.

At block 1180, the hands are aligned automatically based on the tracker data. As noted, the tracker data tracks each movement of the hands. This enables the system to recreate the accurate expected location of the hands, even if the system has been misaligned because it was dropped or experienced some other issue.

At block 1190, once the hands are aligned, the hands are automatically moved to the current time location, based on data from the host device. The host device may obtain clock information via a cellular network, global positioning system, wireless network, Internet connection or through some other means. This data is used to reset the hands of the smart watch. The process then returns to block 1130, to continue controlling the hands of the device using micromotors.

In one embodiment, the tracker uses markings on the dial or hand, to track movements. By using such a tracker system, enabled by the processor and other elements present in a smart watch, the frustrating resetting of a clock display is avoided.

One of ordinary skill in the art will recognize that the processes described in the above flowcharts are conceptual representations of the operations used. The specific operations of the processes may not be performed in the order shown and described. For example and in one embodiment, the process is interrupt driven, rather than sequentially testing for various occurrences. In one embodiment, data is received or processed in a different order. The specific operations may not be performed in one continuous series of operations, and different specific operations may be performed in different embodiments. Additional operations may be performed, or some operations may be skipped. Furthermore, the processes could be implemented using several sub-processes, or as part of a larger macro process. For instance, in some embodiments, the processes shown in these flowcharts are performed by one or more software applications that execute on one or more computing devices.

Figure 12:
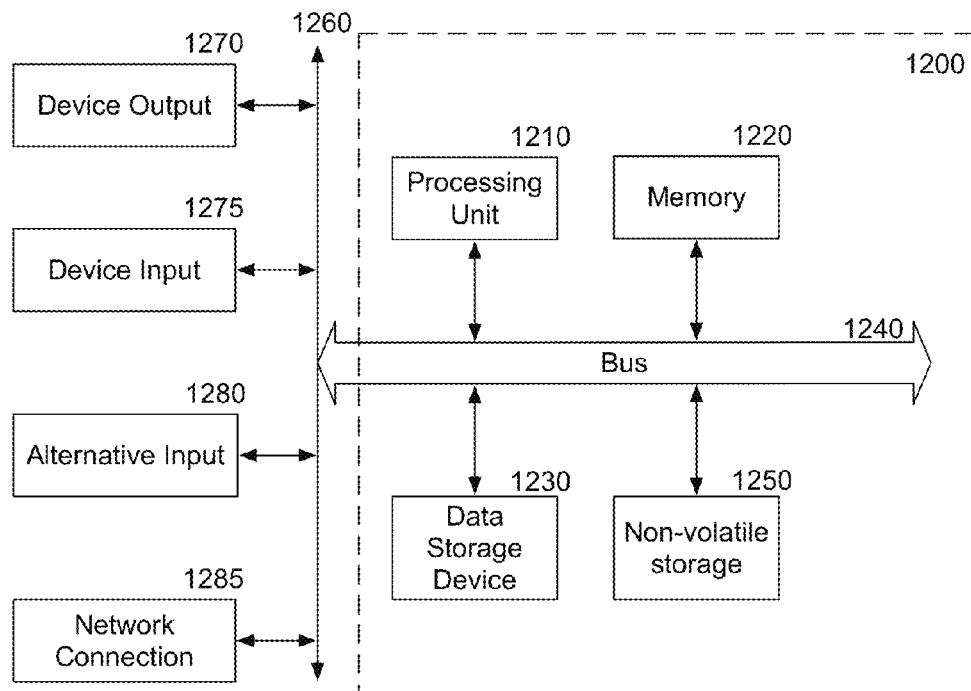
FIG. 12 is a block diagram of one embodiment of a computer system that may be part of the present invention.

FIG. 12 is a block diagram of one embodiment of a computer system that may be part of the present invention. FIG. 12 is a block diagram of a particular machine that may be used with the present invention. It will be apparent to those of ordinary skill in the art, however that other alternative systems of various system architectures may also be used.

The data processing system illustrated in FIG. 12 includes a bus or other internal communication means 1240 for communicating information, and a processing unit 1210 coupled to the bus 1240 for processing information. The processing unit 1210 may be a central processing unit (CPU), a digital signal processor (DSP), or another type of processing unit 1210.

The system further includes, in one embodiment, a random access memory (RAM) or other volatile storage device 1220 (referred to as memory), coupled to bus 1240 for storing information and instructions to be executed by processor 1210. Main memory 1220 may also be used for storing temporary variables or other intermediate information during execution of instructions by processing unit 1210.

The system also comprises in one embodiment a read only memory (ROM) 1250 and/or static storage device 1250 coupled to bus 1240 for storing static information and instructions for processor 1210. In one embodiment the system also includes a data storage device 1230 such as a magnetic disk or optical disk and its corresponding disk drive, or Flash memory or other storage which is capable of storing data when no power is supplied to the system. Data storage device 1230 in one embodiment is coupled to bus 1240 for storing information and instructions.

The system may further be coupled to an output device 1270, such as a cathode ray tube (CRT) or a liquid crystal display (LCD) coupled to bus 1240 through bus 1260 for outputting information. The output device 1270 may be a visual output device, an audio output device, and/or tactile output device (e.g. vibrations, etc.)

An input device 1275 may be coupled to the bus 1260. The input device 1275 may be an alphanumeric input device, such as a keyboard including alphanumeric and other keys, for enabling a user to communicate information and command selections to processing unit 1210. An additional user input device 1280 may further be included. One such user input device 1280 is cursor control device 1280, such as a mouse, a trackball, stylus, cursor direction keys, or touch screen, may be coupled to bus 1240 through bus 1260 for communicating direction information and command selections to processing unit 1210, and for controlling movement on display device 1270.

Another device, which may optionally be coupled to computer system 1200, is a network device 1285 for accessing other nodes of a distributed system via a network. The communication device 1285 may include any of a number of commercially available networking peripheral devices such as those used for coupling to an Ethernet, token ring, Internet, or wide area network, personal area network, wireless network or other method of accessing other devices. The communication device 1285 may further be a null-modem connection, or any other mechanism that provides connectivity between the computer system 1200 and the outside world.

Note that any or all of the components of this system illustrated in FIG. 12 and associated hardware may be used in various embodiments of the present invention.

In one embodiment, the band may include a subset of these elements, such as a processor, flash memory, input/output mechanism, and communications mechanism. The host device may include a subset of superset of these elements, but at least a processing device and a communication device.

It will be appreciated by those of ordinary skill in the art that the particular machine that embodies the present invention may be configured in various ways according to the particular implementation. The control logic or software implementing the present invention can be stored in main memory 1220, mass storage device 1230, or other storage medium locally or remotely accessible to processor 1210.

It will be apparent to those of ordinary skill in the art that the system, method, and process described herein can be implemented as software stored in main memory 1220 or read only memory 1250 and executed by processor 1210. This control logic or software may also be resident on an article of manufacture comprising a computer readable medium having computer readable program code embodied therein and being readable by the mass storage device 1230 and for causing the processor 1210 to operate in accordance with the methods and teachings herein.

The present invention may also be embodied in a handheld or portable device containing a subset of the computer hardware components described above. For example, the handheld device may be configured to contain only the bus 1240, the processor 1210, and memory 1250 and/or 1220.

The handheld device may be configured to include a set of buttons or input signaling components with which a user may select from a set of available options. These could be considered input device #1 1275 or input device #2 1280. The handheld device may also be configured to include an output device 1270 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 1210, a data storage device 1230, a bus 1240, and memory 1220, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1285.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1210. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In one embodiment, the host device is computer system with the expert system and analysis performed by a processor, DSP, or similar processing-capable device. In one embodiment, the host and/or band may include multiple processors, such as a low power processor and a high power processor. In one embodiment, the sensors may be separately powered as well.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A smart watch in a watch case comprising:
at least one sensor within the watch case to track a user's movements;
a processor within the watch case to process data from the at least one sensor, and determine information about the user, based on the user's movements;
a watch face including a subdial to display information about the user, the information calculated by the processor, wherein the information comprises one of: user activity information and user sleep information.

2. The smart watch of claim 1, wherein the subdial includes one or more hands pointing to a number or symbol.

3. The smart watch of claim 1, further comprising:
a communication system to pair the smart watch to a host device, the host device and the smart watch both providing information to the user.

4. The smart watch of claim 3, wherein the pairing of the smart watch and the host device comprises one of: a continuous low power connection, a periodic connection, and an on-demand connection, to share data.

5. The smart watch of claim 3, wherein the host device provides a user interface, enabling a user to set preferences.

6. The smart watch of claim 1, wherein the subdial displays one or more of: a percentage of a step goal currently reached, a percentage of a sleep goal currently reached, a number of steps taken, a number of hours slept, a watch state selected from among awake, asleep, and active.

7. The smart watch of claim 1, further comprising:
a communication system to share sensor data between the smart watch and a host device; and
sensor processing system to analyze the sensor data to determine the user's state and identify user state changes.

8. The smart watch of claim 1, further comprising:
a tracker to track movement of hands on the dial, indicating time, the tracker used to enable automatic realignment of the hands by tracking each motion of the hands and comparing the motion against an actual change in time based on data from a host device.

9. The smart watch of claim 1, further comprising:
the watch face including hands showing time;
one or more micromotors to move the hands in the watch face.

10. The smart watch of claim 9, further comprising:
the one or more micromotors further to move hands on the subdial.

11. The smart watch of claim 10, wherein the watch face including the subdial appears as an analog dial.

12. The smart watch of claim 9, further comprising:
a tracker to track movement of the hands, and determine whether the movements are caused by the micromotors, and when the movement is not caused by the micromotors, the tracker to trigger a reset.

13. A smart watch system including a smart watch, the smart watch comprising:
a sensor to track motion data;
a processor within the smart watch to process data from the at least one sensor, and determine user status information based on the motion data;
a first analog dial face to show time;
a subdial to display the user status information.

14. The smart watch system of claim 13, further comprising:
a micro motor to move hands on the analog dial face.

15. The smart watch system of claim 14, further comprising:
a tracker to track movement of hands on the dial indicating time, the tracker used to enable automatic realignment of the hands by tracking each motion of the hands and comparing the motion against an actual change in time based on data from a host device.

16. The smart watch system of claim 15, wherein the tracked movement data from the tracker is used to realign the hands after a reset.

17. The smart watch system of claim 13, further comprising:
a communication system to pair the smart watch to the host device, the host device and the smart watch both displaying information to the user.

18. The smart watch system of claim 13, wherein the user status information is one of: a percentage of a step goal currently reached or a percentage of a sleep goal currently reached.

19. A smart watch system comprising:
at least one sensor within a watch case to track a user's movements;
a processor within the watch case to process data from the at least one sensor, and determine information about the user, based on the user's movements;

a first watch face to display time; and a second watch face to display information about the user, the information calculated by the processor, wherein the information comprises one of: user activity information and user sleep information.

20. The smart watch system of claim 19, wherein the first watch face and the second watch face are displayed concurrently.

\* \* \* \* \*